(12) United States Patent
Zhu et al.

(10) Patent No.: US 11,234,323 B2
(45) Date of Patent: Jan. 25, 2022

(54) SYSTEMS AND METHODS FOR MEDICAL IMAGING

(71) Applicant: SHANGHAI UNITED IMAGING HEALTHCARE CO., LTD., Shanghai (CN)

(72) Inventors: Guoping Zhu, Shanghai (CN); Patrick Joseph Kling, Houston, TX (US); Jiawen Zhou, Shanghai (CN); Tieshan Zhang, Shanghai (CN); Jinglin Wu, Shanghai (CN); Xu Chu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 148 days.

(21) Appl. No.: 16/656,507

(22) Filed: Oct. 17, 2019

(65) Prior Publication Data
US 2020/0413525 A1 Dec. 31, 2020

(30) Foreign Application Priority Data
Jun. 27, 2019 (CN) .......................... 201910570191.8

(51) Int. Cl.
*H05G 1/32* (2006.01)
*H05G 1/34* (2006.01)
(Continued)

(52) U.S. Cl.
CPC .............. *H05G 1/58* (2013.01); *A61B 5/055* (2013.01); *A61B 6/032* (2013.01); *A61B 6/037* (2013.01);
(Continued)

(58) Field of Classification Search
CPC ......... A61B 5/055; A61B 6/032; A61B 6/037; A61B 6/40; A61B 6/482; A61B 6/542; A61B 6/4417; A61B 6/025; A61B 6/035; A61B 6/0492; A61B 6/4085; A61B 6/4208; A61B 6/4258; A61B 6/4435; A61B 6/4233; A61B 8/4416; A61B 6/405; A61B 6/481; A61B 6/5217; A61B 6/54;
(Continued)

(56) References Cited

U.S. PATENT DOCUMENTS 4,573,184 A * 2/1986 Tanaka ...................... H05G 1/34
363/28
4,710,860 A * 12/1987 Tsuchiya .................. H05G 1/32
363/28
(Continued)

FOREIGN PATENT DOCUMENTS

CN 101356492 A 1/2009

*Primary Examiner* — Irakli Kiknadze
(74) *Attorney, Agent, or Firm* — Metis IP LLC

(57) ABSTRACT

Systems and methods for medical imaging. The method may include acquiring a tube voltage switching waveform for a radiation source of a medical device. The method may include determining a tube current switching period based on the tube voltage switching waveform. The method may include determining a sampling period correlated with the tube current switching period. The method may include acquiring projection data according to the sampling period. The method may further include reconstructing an image based on the acquired projection data.

20 Claims, 13 Drawing Sheets

(51) Int. Cl.
*A61B 6/00* (2006.01)
*H05G 1/58* (2006.01)
*A61B 5/055* (2006.01)
*A61B 6/03* (2006.01)
*G06T 7/00* (2017.01)
*G06T 11/00* (2006.01)
*H01J 35/02* (2006.01)

(52) U.S. Cl.
CPC ............. *A61B 6/40* (2013.01); *A61B 6/542* (2013.01); *G06T 7/0012* (2013.01); *G06T 11/003* (2013.01); *H01J 35/025* (2013.01)

(58) Field of Classification Search
CPC ..... A61B 6/452; G06T 11/003; G06T 11/005; G06T 2211/408; G06T 7/0012; H01J 35/025; H01J 35/045; H01J 35/147; H01J 35/153; H01J 2235/081; H01J 2235/086; H01J 35/065; H01J 35/10; H01J 35/14; H05G 1/085; H05G 1/265; H05G 1/58; H05G 1/02; H05G 1/10; H05G 1/22; H05G 1/32; H05G 1/50; H05G 1/52; H05G 1/64; H05G 1/08; H05G 1/54; H05G 1/56; H05G 1/18; H05G 1/24; G01N 23/046; G01N 2223/04; G01N 2223/1016; G01N 2223/304; G01N 2223/419; G01N 23/083; G01N 2223/505; G01N 2223/108; G01N 23/2255; G01T 1/242; G01T 1/248; G01T 1/2018; G01T 1/202; G01T 1/2971; G01T 1/22; G01T 1/2985; G21K 1/043; G21K 1/025; A61N 2005/1061; A61N 2005/1097; A61N 5/10; A61N 5/1037; A61N 5/1049; A61N 5/1068; G16H 50/30
USPC .................. 378/109–111, 114, 119, 4–19
See application file for complete search history.

(56) References Cited

U.S. PATENT DOCUMENTS 5,994,852 A * 11/1999 Lee .................. H04N 3/27
 315/408
2013/0251108 A1* 9/2013 Luerkens ............ H05G 1/58
 378/106

\* cited by examiner

SYSTEMS AND METHODS FOR MEDICAL IMAGING

CROSS-REFERENCE TO RELATED APPLICATIONS

This application claims priority to Chinese Patent Application No. 201910570191.8 filed on Jun. 27, 2019, the contents of which are incorporated herein by reference.

TECHNICAL FIELD

The present disclosure generally relates to medical imaging, and more particularly, systems and methods for an energy imaging based on fast tube voltage (kV) switching.

BACKGROUND

With the extensive development of modern medical imaging technology, a density image of voxels obtained by a conventional computed tomography (CT) may not be able to identify a substance differentiation accurately. To resolve the issue, an energy imaging technology based on fast tube voltage (kV) switching is developed, which can accurately identify different voxel substances. During a dual energy imaging, a high energy kV and a low energy kV may be switched quickly, which may facilitate to obtain simultaneous homologous data domain energy imaging. In clinical applications, the energy imaging is an attractive imaging technology.

During the dual energy imaging, the ideal kV switching waveform should be a square waveform (or a rectangular waveform), which has the highest spectral energy separation capability and the best image quality. However, the limitations of actual physical conditions (e.g., output capacitances of a high voltage generator (HVG) and a high voltage (HV) cable), result in the transition time during which the kV switches from the high energy kV and the low energy kV. The shorter the transition time, the better the spectral energy separation capability, and the better the image quality of the energy imaging.

Since the transition time (e.g., kV fall time) is directly related to the tube current (mA) and the output capacitance of the HVG. The mV is used to discharge the output capacitance of the HVG to achieve the reduction of the kV. In some cases, if the output capacitance is fixed, high mV can be usually used to reduce the kV fall time. While high mA can bring a high scan dose, which is harmful to the subject. Therefore, it is desirable to develop systems and methods for energy imaging having a low scan dose.

SUMMARY

According to a first aspect of the present disclosure, a method is provided. The method may include one or more operations. The one or more operations may be implemented on a computing device having at least one processor and at least one computer-readable storage medium. The at least one processor may acquire a tube voltage switching waveform for a radiation source of a medical device. The tube voltage switching waveform may be configured to direct an alternation between a high energy tube voltage and a low energy tube voltage that are applied to the radiation source. The at least one processor may determine a tube current switching period based on the tube voltage switching waveform. The tube current switching period may be indicative of an on-off state of the tube current applied to the radiation source. The at least one processor may determine a sampling period correlated with the tube current switching period. The at least one processor may acquire projection data according to the sampling period. The projection data may include first projection data under the high energy tube voltage and second projection data under the low energy tube voltage, and the projection data may be generated according to the on-off state of a tube current indicated by the tube current switching period. The at least one processor may reconstruct an image based on the acquired projection data.

In some embodiments, the alternation between a high energy tube voltage and a low energy tube voltage may be represented by a rising edge, a falling edge, a low energy voltage plateau duration and a high energy voltage plateau duration of the tube voltage switching waveform. The on-off state of the tube current may include an on-stage of the tube current switching period and an off-stage of the tube current switching period. The on-stage and the off-stage may alternate.

In some embodiments, the at least one processor may determine that the tube current is within the on-stage of the tube current switching period in response to occurrence of the falling edge of the tube voltage.

In some embodiments, the at least one processor may determine that the tube current is within the off-stage of the tube current period in response to occurrence of the tube voltage between a first predetermined time of the low energy voltage plateau duration and a second predetermined time of the low energy voltage plateau duration.

In some embodiments, the at least one processor may determine that the tube current is within the off-stage of the tube current period in response to occurrence of the tube voltage between a third predetermined time of the low energy voltage plateau duration and a fourth predetermined time of the rising edge.

In some embodiments, the at least one processor may determine that the tube current is within the off-stage of the tube current period in response to occurrence of the tube voltage between a fifth predetermined time of the low energy voltage plateau duration and a sixth predetermined time of the high energy voltage plateau duration.

In some embodiments, the at least one processor may determine that the tube current is within the off-stage of the tube current period in response to occurrence of the tube voltage between a seventh predetermined time of the high energy voltage plateau duration and an eighth predetermined time of the high energy voltage plateau duration.

In some embodiments, the off-stage of the tube current switching period may include a short off-stage and a long off-stage. The at least one processor may determine that the tube current is on the short off-stage in response to occurrence of the tube voltage between a ninth predetermined time of the rising edge and a tenth predetermined time of the rising edge. The at least one processor may determine that the tube current is within the long off-stage in response to occurrence of the tube voltage between an eleventh predetermined time of the low energy voltage plateau duration and a twelfth predetermined time of the low energy voltage plateau duration.

In some embodiments, the at least one processor may determine, based on the on-off state of the tube current, a sampling on-stage and a sampling off-stage respectively. The sampling on-stage may include at least part of the time duration corresponding to the on-stage of the tube current switching period.

In some embodiments, the at least one processor may determine that the sampling off-stage is between a thirteenth predetermined time of the low energy voltage plateau duration and a fourteenth predetermined time of the low energy voltage plateau duration.

In some embodiments, the at least one processor may determine that the sampling off-stage is between a fifteenth predetermined time of the falling edge and a sixteenth predetermined time of the low energy voltage plateau duration.

In some embodiments, the at least one processor may determine that the sampling off-stage is between a seventh predetermined time of the low energy voltage plateau duration and an eighteenth predetermined time of the rising edge.

In some embodiments, the at least one processor may determine that the sampling off-stage is between a nineteenth predetermined time of the high energy voltage plateau duration and a twentieth predetermined time of the falling edge.

In some embodiments, the at least one processor may determine that the sampling off-stage is between a twenty-first predetermined time of the high energy voltage plateau duration and a twenty-second predetermined time of the falling edge.

In some embodiments, the sampling off-stage may include a short sampling off-stage and a long sampling off-stage. The at least one processor may determine that the short sampling off-stage is between a twenty-third predetermined time of the rising edge and a twenty-fourth predetermined time of the rising edge. The at least one processor may determine that the long sampling off-stage is between a twenty-fifth predetermined time of the falling edge and a twenty-sixth predetermined time of the low energy voltage plateau duration.

According to a second aspect of the present disclosure, an imaging system may be provided. The imaging system may include at least one storage medium including a set of instructions for reconstructing a computed tomography (CT) image, and at least one processor in communication with the at least one storage medium. When executing the set of instructions, the at least one processor may cause the imaging system to perform one or more operations. The at least one processor may acquire a tube voltage switching waveform for a radiation source of a medical device. The tube voltage switching waveform may be configured to direct an alternation between a high energy tube voltage and a low energy tube voltage that are applied to the radiation source. The at least one processor may determine a tube current switching period based on the tube voltage switching waveform. The tube current switching period may be indicative of an on-off state of the tube current applied to the radiation source. The at least one processor may determine a sampling period correlated with the tube current switching period. The at least one processor may acquire projection data according to the sampling period. The projection data may include first projection data under the high energy tube voltage and second projection data under the low energy tube voltage, and the projection data may be generated according to the on-off state of a tube current indicated by the tube current switching period. The at least one processor may reconstruct an image based on the acquired projection data.

According to a third aspect of the present disclosure, a non-transitory computer readable medium embodying a computer program product may be provided. The computer program product may comprise instructions configured to cause a computing device to perform one or more operations. The computing device may acquire a tube voltage switching waveform for a radiation source of a medical device. The tube voltage switching waveform may be configured to direct an alternation between a high energy tube voltage and a low energy tube voltage that are applied to the radiation source. The computing device may determine a tube current switching period based on the tube voltage switching waveform. The tube current switching period may be indicative of an on-off state of the tube current applied to the radiation source. The computing device may determine a sampling period correlated with the tube current switching period. The computing device may acquire projection data according to the sampling period. The projection data may include first projection data under the high energy tube voltage and second projection data under the low energy tube voltage, and the projection data may be generated according to the on-off state of a tube current indicated by the tube current switching period. The computing device may reconstruct an image based on the acquired projection data.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by other expression if they achieve the same purpose.

Figure 3:
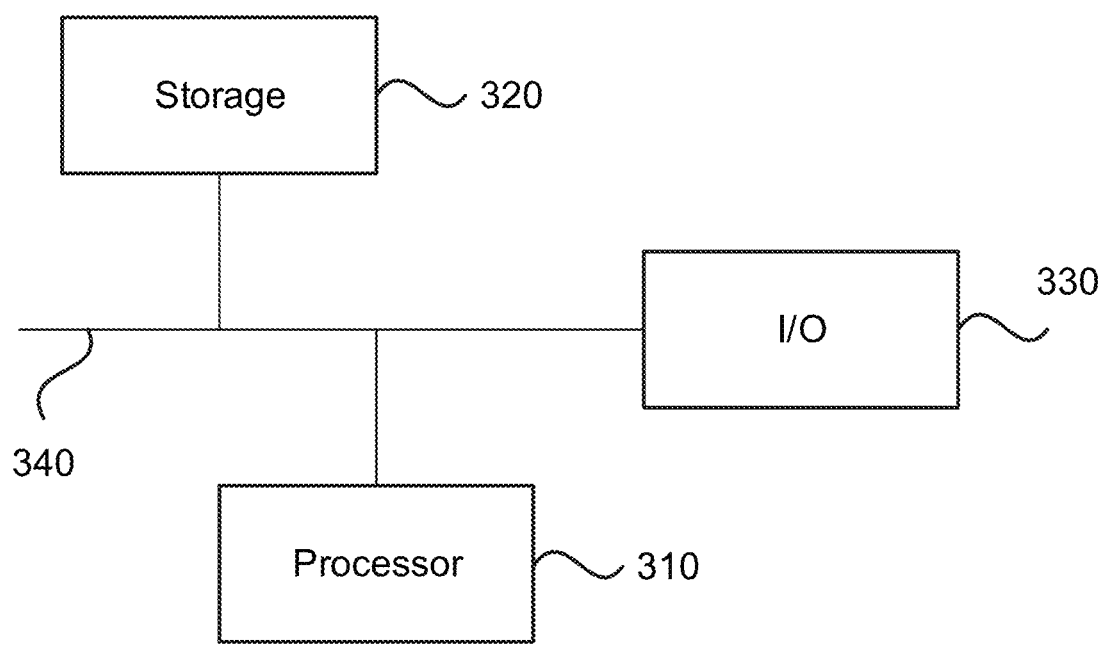
FIG. 3 is a schematic diagram illustrating hardware and/or software components of an exemplary computing device according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under the guidance of the present disclosure. Those variations, changes and/or modifications do not depart from the scope of the present disclosure.

Figure 1:
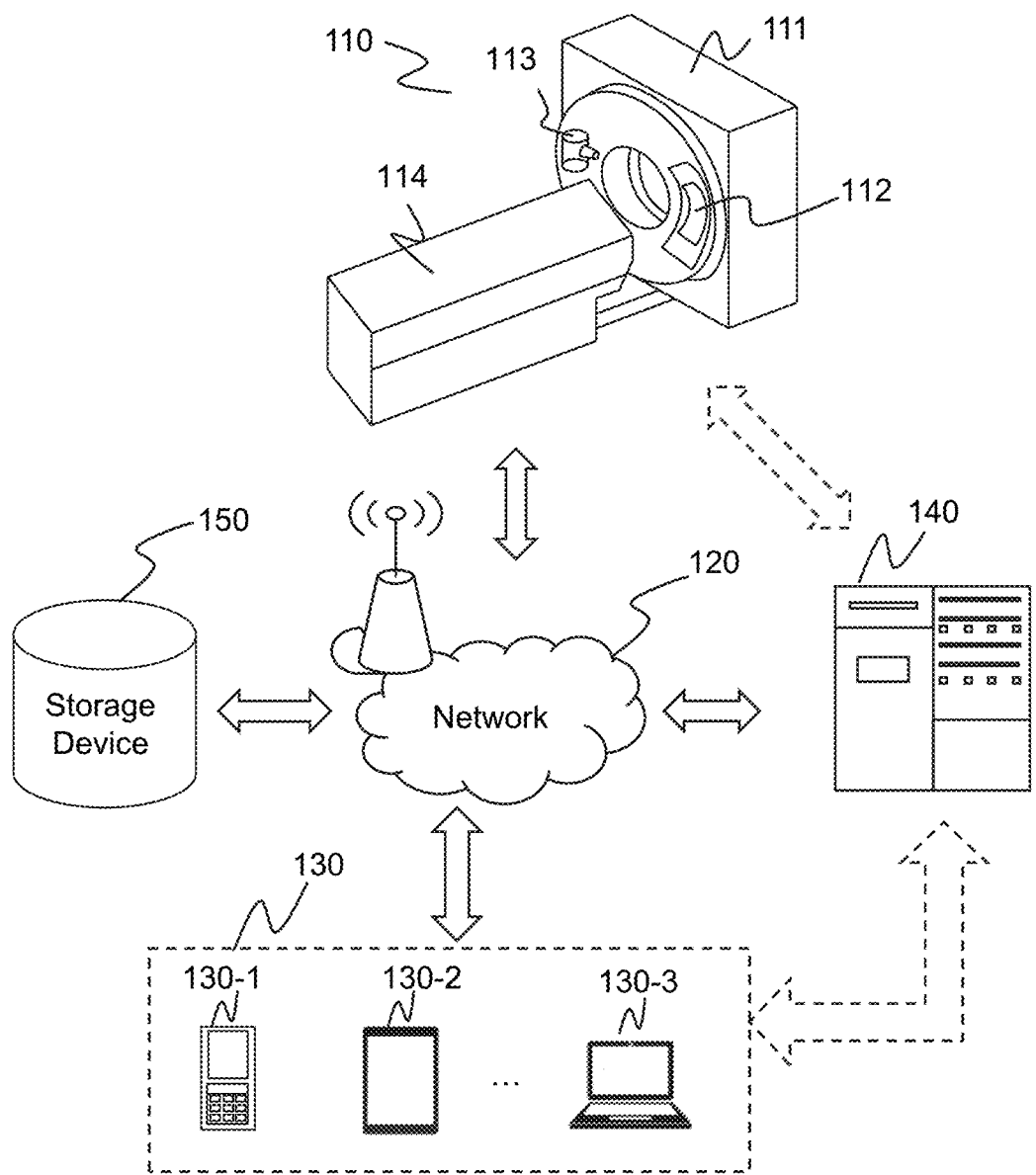
FIG. 1 is a schematic diagram illustrating an exemplary imaging system according to some embodiments of the present disclosure.

FIG. 1 is a schematic diagram illustrating an exemplary imaging system according to some embodiments of the present disclosure. As illustrated in FIG. 1, the imaging system 100 may include an imaging device 110, a network 120, one or more terminals 130, a processing device 140, and a storage device 150. The components in the imaging system 100 may be connected in one or more of various ways. Merely by way of example, the imaging device 110 may be connected to the processing device 140 through the network 120. As another example, the imaging device 110 may be connected to the processing device 140 directly as indicated by the bi-directional arrow in dotted lines linking the imaging device 110 and the processing device 140. As a further example, the storage device 150 may be connected to the processing device 140 directly or through the network 120. As still a further example, the one or more terminals 130 may be connected to the processing device 140 directly (as indicated by the bi-directional arrow in dotted lines linking the terminal 130 and the processing device 140) or through the network 120.

In some embodiments, the imaging device 110 may include a computed tomography (CT) scanner, a positron emission tomography (PET) scanner, a magnetic resonance imaging (MRI) scanner, a multi-modality scanner, or the like, or a combination thereof. Exemplary CT scanner may include a Multi-detector computed tomography (MDCT), a Multi-slice computed tomography (MSCT), or the like, or any combination thereof. Exemplary multi-modality scanners may include a computed tomography-positron emission tomography (CT-PET) scanner, a computed tomography-magnetic resonance imaging (CT-MRI) scanner, or the like, or any combination thereof.

Taking a CT scanner as an example, the imaging device 110 may include a gantry 111, a detector 112, a radiation source 113, and a scanning table 114. The detector 112 and the radiation source 113 may be oppositely mounted on the gantry 111. A scan object may be placed on the scanning table 114 and moved into a detection tunnel (e.g., a space between the detector 112 and the radiation source 113) of the imaging device 110. The scan object may be biological or non-biological. Merely by way of example, the scan object may include a patient, a man-made object, etc. As another example, the scan object may include a specific portion, organ, and/or tissue of the patient. For example, the scan object may include head, brain, neck, body, shoulder, arm, thorax, cardiac, stomach, blood vessel, soft tissue, knee, feet, or the like, or any combination thereof. In the present disclosure, "subject", "object" or "scan object" are used interchangeably.

The radiation source 113 may emit radiation rays to scan the scan object that is placed on the scanning table 114. The radiation rays may include X-rays, γ-rays, α-rays, ultraviolet, laser, neutron, proton, or the like, or a combination thereof. The detector 112 may receive the radiation rays passed through the scan object. In some embodiments, the detector 112 may include a plurality of detector units, which may be arranged in a channel direction and a row direction. The detector 112 may include a scintillation detector (e.g., a cesium iodide detector) or a gas detector. More descriptions of the radiation source 113 may be found elsewhere in the present disclosure (e.g., FIG. 2 and the descriptions thereof).

The network 120 may facilitate exchange of information and/or data. In some embodiments, one or more components of the imaging system 100 (e.g., the imaging device 110, the terminal 130, the processing device 140, or the storage device 150) may send information and/or data to another component(s) in the imaging system 100 via the network 120. For example, the processing device 140 may obtain, via the network 120, an image from the storage device 150. In some embodiments, the network 120 may be any type of wired or wireless network, or combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, an optical fiber network, a telecommunications network, an intranet, an Internet, a local area network (LAN), a wide area network (WAN), a wireless local area network (WLAN), a metropolitan area network (MAN), a wide area network (WAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired or wireless network access points such as base stations and/or internet exchange points through which one or more components of the imaging system 100 may be connected to the network 120 to exchange data and/or information.

The one or more terminals 130 include a mobile device 130-1, a tablet computer 130-2, a laptop computer 130-3, or the like, or any combination thereof. In some embodiments, the mobile device 130-1 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, an accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google Glass, an Oculus Rift, a HoloLens, a Gear VR, etc. In some embodiments, the one or more terminals 130 may remotely operate the imaging device 110. In some embodiments, the one or more terminals 130 may operate the imaging device 110 via a wireless connection. In some embodiments, the one or more terminals 130 may receive information and/or instructions inputted by a user, and send the received information and/or instructions to the imaging device 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

In some embodiments, the processing device 140 may process data obtained from the imaging device 110, the one or more terminals 130, or the storage device 150. For example, the processing device 140 may determine a tube current (mA) switching period and/or a sampling period based on a tube voltage (kV) switching waveform. As another example, the processing device 140 may cause, at the direction of the kV switching waveform and the mA switching period, the imaging device 110 to acquire projection data within sampling on-stage(s) of the sampling period. As a further example, the processing device 140 may reconstruct an image (e.g., a CT image) based on collected projection data. The processing device 140 may be a central processing unit (CPU), a digital signal processor (DSP), a system on a chip (SoC), a microcontroller unit (MCU), or the like, or any combination thereof.

In some embodiments, the processing device 140 may be a single server or a server group. The server group may be centralized or distributed. In some embodiments, the processing device 140 may be local or remote. For example, the processing device 140 may access information and/or data stored in the imaging device 110, the one or more terminals 130, and/or the storage device 150 via the network 120. As another example, the processing device 140 may be directly connected to the imaging device 110, the one or more terminals 130, and/or the storage device 150, to access stored information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the one or more terminals 130 and/or the processing device 140. For example, the storage device 150 may store scan parameters for directing the imaging device 110 to scan the subject. The scan parameters may include a tube voltage (kV), a tube current (mA), a sampling period, an exposure time, a scan region, etc. In some embodiments, the storage device 150 may store data and/or instructions that the processing device 140 may execute or use to perform exemplary methods described in the present disclosure. For example, the storage device 150 may store data and/or instructions that the processing device 140 may execute or use to reconstruct a medical image. As another example, the storage device 150 may store data and/or instructions that the processing device 140 may execute or use to apply suitable tube voltage and/or tube current to the imaging device 110. In some embodiments, the storage device 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the terminal 130, the processing device 140). One or more components of the imaging system 100 may access the data or instructions stored in the storage device 150 via the network 120. In some embodiments, the storage device 150 may be directly connected to or communicate with one or more components of the imaging system 100 (e.g., the terminal 130, the processing device 140). In some embodiments, the storage device 150 may be part of the processing device 140.

Figure 2:
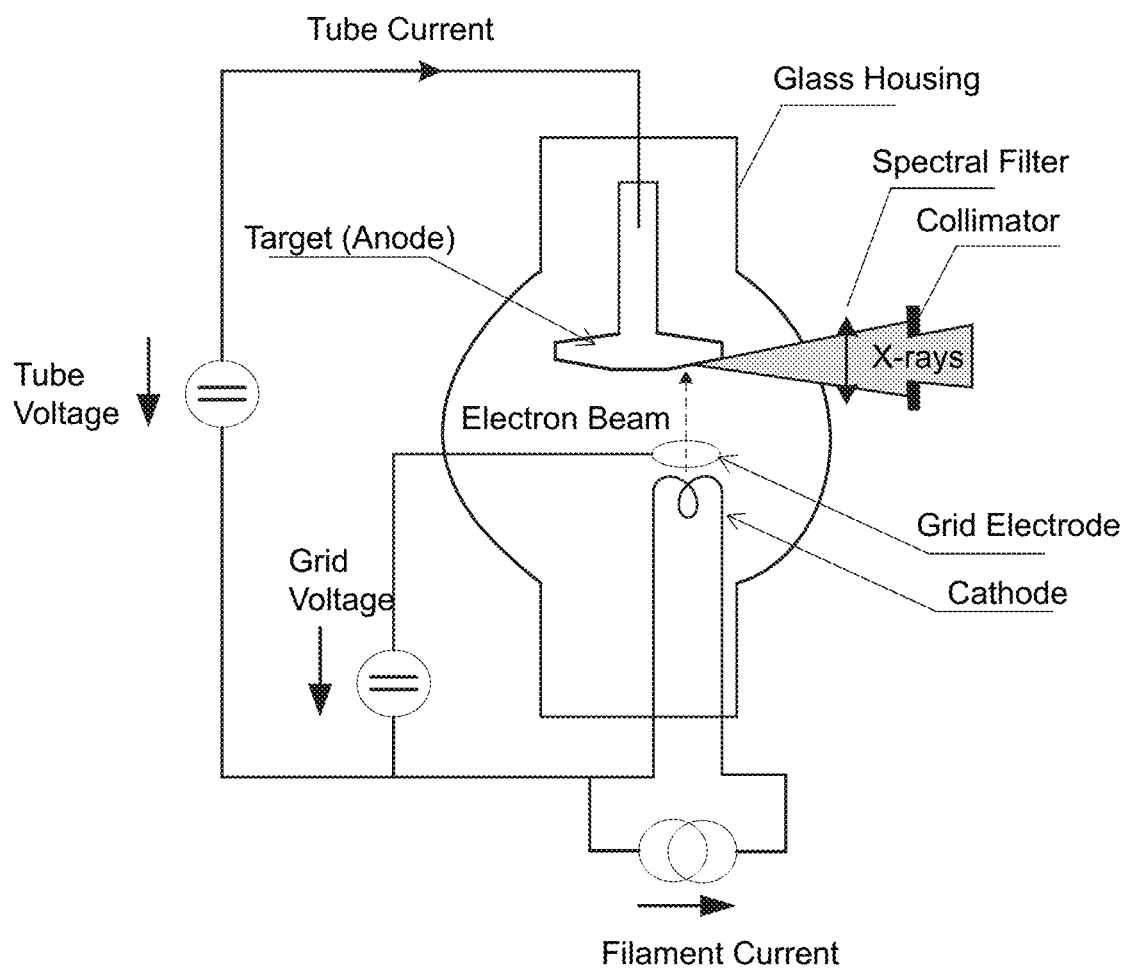
FIG. 2 is a schematic diagram illustrating exemplary components of a radiation source according to some embodiments of the present disclosure.

FIG. 2 is a schematic diagram illustrating exemplary components of a radiation source according to some embodiments of the present disclosure. As used herein, typical radiation source 113 may include an X-ray tube for emitting X-rays. As shown in FIG. 2, the X-ray tube may include a cathode, an anode, a grid electrode, a spectral filter, a collimator, etc. In some embodiments, the cathode may include filament(s) for emitting electrons. The anode may include a target for receiving the electrons emitted by the cathode. X-rays may be generated when the electrons strike to the target. The grid electrode may be provided to the cathode to control discharge of the electrons emitted by the cathode. The tube current (mA) of the X-ray tube may be switched on or off based on a control of the grid electrode. For example, when the grid voltage of the grid electrode is maintained at zero value or about zero value, the electron emission of the cathode filament is allowed and the mA is switched on. When the grid voltage is maintained at a negative cut-off voltage, the electron emission of the cathode filament is stopped and the mA is switched off. In some embodiments, the anode may be located opposite to the cathode. The grid electrode may be located in the proximity of the cathode. In some embodiments, one or more control circuits may be applied to the anode, the cathode and/or the grid electrode so as to control the generation of X-rays. In some embodiments, the anode, the cathode and the grid electrode may be enclosed by a glass housing. A vacuum environment may be formed in the glass housing.

In some embodiments, the cathode may be heated to emit an electron beam (that is composed of a great number of electrons) in the vacuum by passing a current through the filament (e.g., filament current). Then the negatively charged electron beam can be accelerated towards the anode/target under a certain tube voltage (e.g., a high energy kV or a low energy kV). The tube current, mA, may be formed due to the acceleration of the electron beam. In some embodiments, the high energy kV, $kV_h$, typically in the range of 120-150 kV, and the low energy kV, $kV_l$, typically in the range of 70-100 kV. The kV$_h$ and kV$_l$ may be switched according to a kV switching waveform. In some embodiments, in response to a control of grid voltage of the grid electrode, when the electron beam strikes to the target, the X-rays can be generated. The X-rays may pass through a predefined relatively small output window (not shown in FIG. 2). In some embodiments, a specific content of the passed X-rays may be selected by a filtration of the spectral filter, and the X-rays may be collimated by the collimator to a required beam size. In some embodiments, the spectral filter and the collimator may be disposed insider or outside of the housing of the X-ray tube.

FIG. 3 is a schematic diagram illustrating hardware and/or software components of an exemplary computing device according to some embodiments of the present disclosure. As illustrated in FIG. 3, the computing device 300 may include a processor 310, a storage 320, an input/output (I/O) 330, and a communication port 340. In some embodiments, the processing device 140 and/or the one or more terminals 130 may be implemented on the computing device 300.

The processor 310 may execute computer instructions (program code) and, when executing the instructions, cause the processing device 140 to perform functions of the processing device 140 in accordance with techniques described herein. The computer instructions may include, for example, routines, programs, objects, components, signals, data structures, procedures, modules, and functions, which perform particular functions described herein. In some embodiments, the processor 310 may process data and/or images obtained from the imaging device 110, the terminal 130, the storage device 150, and/or any other component of the imaging system 100. For example, the processor 310 may acquire projection data from the storage device 150, and reconstruct an image based on the projection data. In some embodiments, the processor 310 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration, only one processor is described in the computing device 300. However, it should be noted that the computing device 300 in the present disclosure may also include multiple processors. Thus operations and/or method steps that are performed by one processor as described in the present disclosure may also be jointly or separately performed by the multiple processors. For example, if in the present disclosure the processor of the computing device 300 executes both process A and process B, it should be understood that process A and process B may also be performed by two or more different processors jointly or separately in the computing device 300 (e.g., a first processor executes process A and a second processor executes process B, or the first and second processors jointly execute processes A and B).

The storage 320 may store data/information obtained from the imaging device 110, the one or more terminals 130, the storage device 150, or any other component of the imaging system 100. In some embodiments, the storage 320 may include a mass storage device, removable storage device, a volatile read-and-write memory, a read-only memory (ROM), or the like, or any combination thereof. For example, the mass storage may include a magnetic disk, an optical disk, a solid-state drive, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure. For example, the storage 320 may store a program (e.g., in the form of computer-executable instructions) for the processing device 140 to determine a tube current switching period and a sampling period based on a tube voltage switching waveform. As another example, the storage 320 may store a program (e.g., in the form of computer-executable instructions) for the processing device 140 to reconstruct an image based on projection data acquired by the imaging device 110.

The I/O 330 may input or output signals, data, and/or information. In some embodiments, the I/O 330 may enable user interaction with the processing device 140. In some embodiments, the I/O 330 may include an input device and an output device. Exemplary input devices may include a keyboard, a mouse, a touch screen, a microphone, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

The communication port 340 may be connected to a network (e.g., the network 120) to facilitate data communications. The communication port 340 may establish connections between the processing device 140 and the imaging device 110, the terminal 130, or the storage device 150. The connection may be a wired connection, a wireless connection, or combination of both that enables data transmission and reception. The wired connection may include an electrical cable, an optical cable, a telephone wire, or the like, or any combination thereof. The wireless connection may include Bluetooth, Wi-Fi, WiMAX, WLAN, ZigBee, mobile network (e.g., 3G, 4G, 5G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
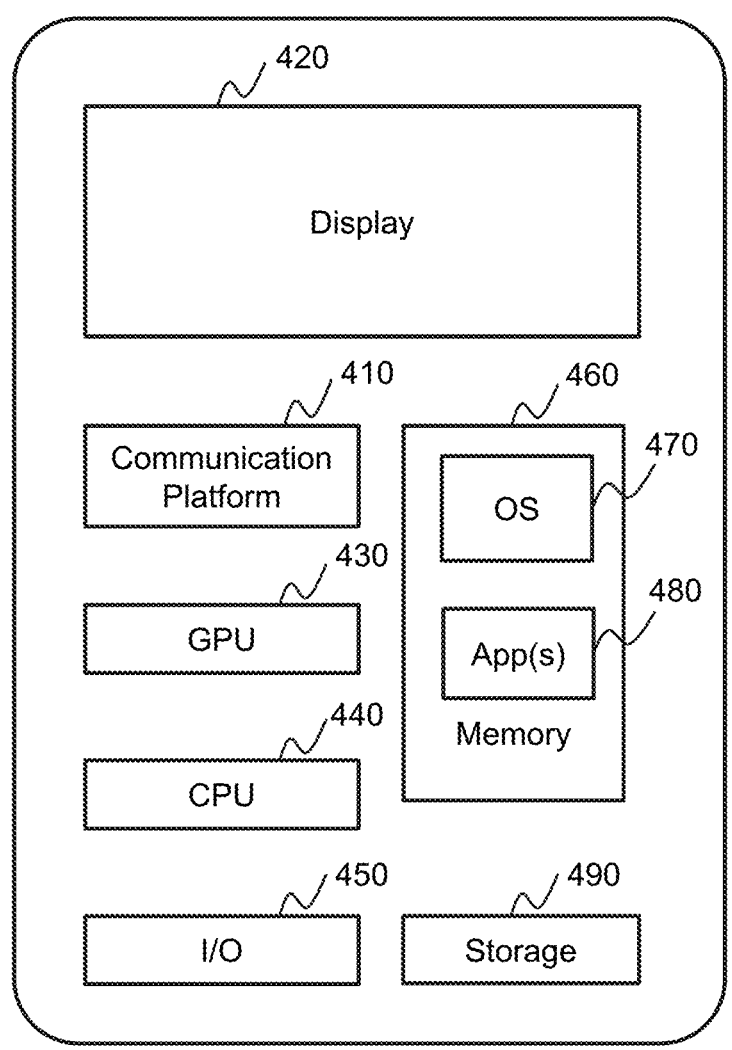
FIG. 4 is a schematic diagram illustrating hardware and/or software components of a mobile device according to some embodiments of the present disclosure.

FIG. 4 is a schematic diagram illustrating hardware and/or software components of a mobile device according to some embodiments of the present disclosure. In some embodiments, the processing device 140 and/or the one or more terminals 130 may be implemented on the mobile device 400. As illustrated in FIG. 4, the mobile device 400 may include a communication platform 410, a display 420, a graphic processing unit (GPU) 430, a central processing unit (CPU) 440, an I/O 450, a memory 460, and a storage 490.

In some embodiments, any other suitable component, including but not limited to a system bus or a controller (not shown), may also be included in the mobile device 400. In some embodiments, a mobile operating system 470 (e.g., iOS, Android, Windows Phone, Harmony OS, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate high-quality image of a scan object as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result, the drawings should be self-explanatory.

In some embodiments, the imaging system 100, such as a dual energy CT (DECT) scan system, may have an energy discriminating, multi-energy, or dual-energy capability. The imaging system 100 may scan the subject with two distinctive energy spectra (e.g., a high energy kV and a low energy kV). The imaging system 100 may provide energy discrimination and material characterization based on low-energy and high-energy portions of incident X-rays. In clinical applications, dual energy CT imaging based on fast kV switching is a competitive energy imaging technology. It requires that the high energy kV ($kV_h$, typically in the range of 120-150 kV) and the low energy kV ($kV_l$, typically in the range of 70-100 kV) can be quickly switched in order to reduce a transition time between $kV_h$ and $kV_l$.

Figure 7A:
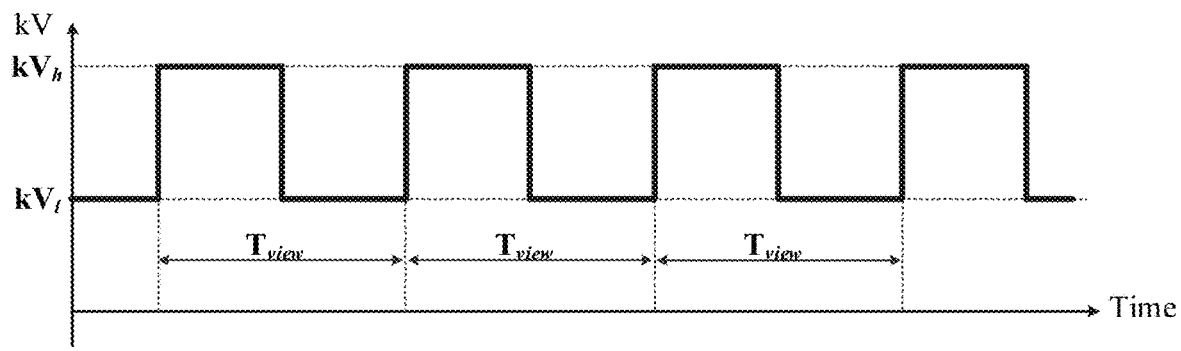
FIG. 7A is a schematic diagram illustrating an ideal tube voltage (kV) switching waveform according to some embodiments of the present disclosure.

FIG. 7A shows an ideal kV switching waveform according to some embodiments of the present disclosure. As shown in FIG. 7A, the ideal kV switching waveform may be composed of square (or rectangular) pluses, which indicates the highest energy separation capability. Hereinafter the projection acquired at $kV_l$ is called a low energy projection, and the projection acquired at $kV_h$ is called a high energy projection. In some embodiments, one energy projection or view may include a high energy projection and/or a low energy projection. As shown in FIG. 7A, one view includes the high energy projection and the low energy projection. In some embodiments, a time duration (e.g., $T_{view}$) of one view may be in the range of several hundreds to several thousands of nanoseconds, such as 100 µs, 200 µs, 300 µs, 400 µs, 500 µs, etc. In some embodiments, the time duration of one view may be predetermined according to the scanning parameters.

As illustrated in FIG. 7A, it is ideal if $kV_h$ falls to $kV_l$ without a transition, or $kV_l$ rises to $kV_h$ without a transition. However, the ideal kV switching is hardly achieved due to the limitations of physical conditions. For a practical imaging system, a high voltage generator (HVG, not shown in FIG. 1 and FIG. 2) should have enough big output capacitance to ensure the kV ripple is small enough, otherwise it may affect an image quality of the CT image. The HVG may be configured to apply kV to the radiation source 113 (e.g., the X-ray tube). The output capacitance of HVG is not unavoidable. Besides, the capacitance of a high voltage (HV) cable connected the HVG and the radiation source 113 can't be avoided as well. Due to the existence of capacitances of the HVG and the HV cable, the output kV of the HVG may not be capable of switching kV between $kV_l$ and $kV_h$ without any transition. Therefore, the ideal square kV switching waveform may be unachievable in a practical imaging system. A finite transition time may be existed for the kV switching.

Figure 7B:
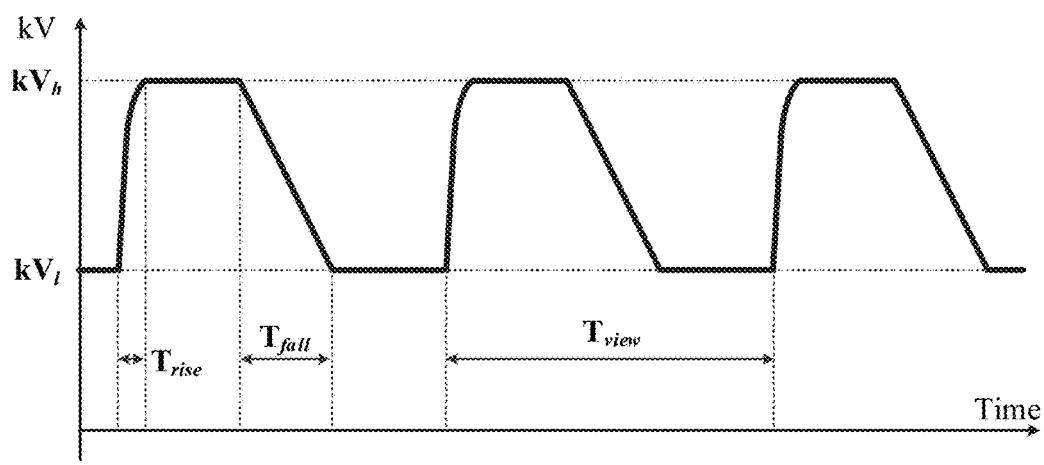
FIG. 7B is a schematic diagram illustrating an actual tube voltage (kV) switching waveform according to some embodiments of the present disclosure.

FIG. 7B shows an actual tube voltage (kV) switching waveform. As shown in FIG. 7B, in the time duration of one view (e.g., $T_{view}$, representing the time duration of one view), either of the time duration of a rising edge (e.g., $T_{rise}$, representing kV rise time or the time duration when the kV is switched from $kV_l$ to $kV_h$) and the time duration of a falling edge ($T_{fall}$, representing kV fall time or the time duration when the kV is switched from $kV_h$ to $kV_l$) may be deemed as the transition time. Due to the limitations of the HVG and the loss in the system, such transition time may be unavoidable. Referring to FIG. 7B, in the time duration of one view, the actual kV switching waveform may include a rising edge, a high energy voltage plateau duration, a falling edge, and a low energy voltage plateau duration. The rising edge corresponds to the kV rise time. The high energy voltage plateau duration corresponds to the time duration when kV stays at $kV_h$. The falling edge corresponds to the kV fall time. The low energy voltage plateau duration corresponds to the time duration when kV stays at $kV_l$.

Figure 7C:
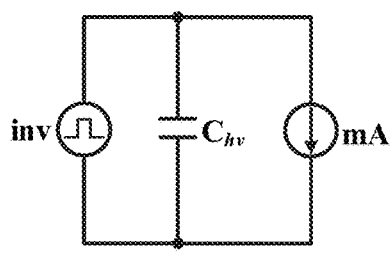
FIG. 7C is a schematic diagram illustrating an equivalent circuit during a kV rise time of a high voltage generator (HVG) according to some embodiments of the present disclosure.

FIG. 7C shows an equivalent circuit during the kV rise time of the HVG. Seen from FIG. 7C, the kV rise time may be not only restricted by the HV capacitance ($C_{hv}$) and the tube current (mA), but also restricted by a power output capability and dynamic response speed of an inverter (inv). It is desirable to achieve a fast response and almost no overshoot for the rising of the kV, but which may need extremely high performance requirements for a control of the HVG. It is hard to achieve the extremely high control accuracy of the HVG in reality. In some embodiments, if the inverter is turned off, an equivalent circuit of the HVG during the kV fall time may be shown in FIG. 7D.

Figure 7D:
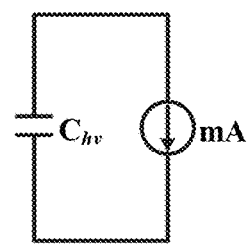
FIG. 7D is a schematic diagram illustrating an equivalent circuit during a kV fall time of a high voltage generator (HVG) according to some embodiments of the present disclosure.

FIG. 7D shows an equivalent circuit during the kV fall time of the HVG. Seen from FIG. 7D, the kV fall time may be restricted by the HV capacitance ($C_{hv}$) and the tube current (mA). Given that $C_{hv}$ is a constant value, thus the kV fall time may only depend on the mA. The larger the mA, the smaller the kV fall time. For dual energy CT imaging based on the fast kV switching, the smaller the kV transition time (e.g., $T_{fall}$ or $T_{rise}$), the better the spectral energy separation capability. In some embodiments, because the kV fall time is totally determined by the mA, a high mA can be used to reduce the kV fall time and improve spectral energy separation.

Figures 8A, 8B:
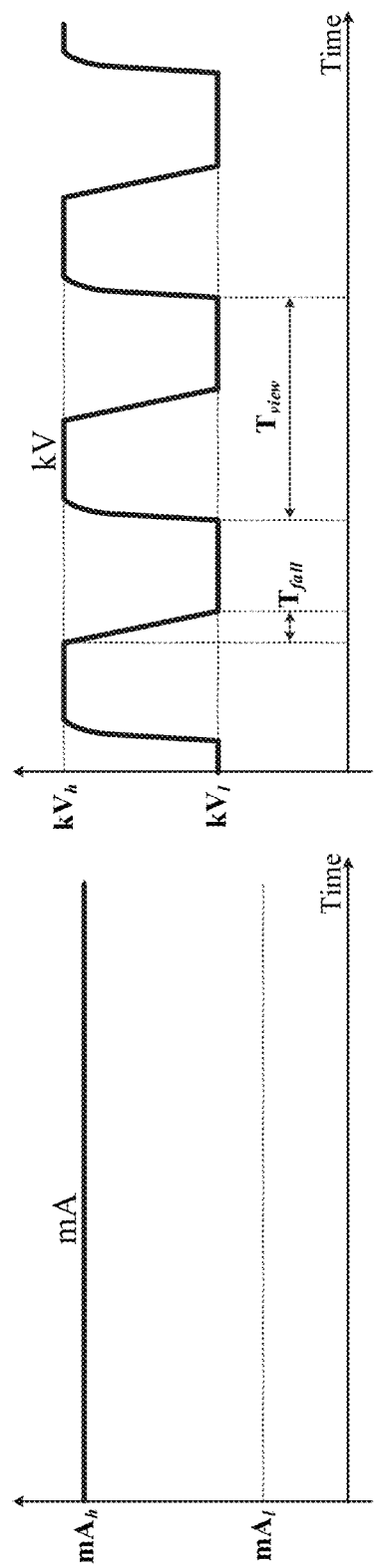
FIG. 8A is a schematic diagram illustrating a constant tube current (mA) continuously applied to a radiation source.
FIG. 8B is a schematic diagram illustrating an actual tube voltage (kV) switching waveform correlated with the constant high mA illustrated in FIG. 8A.

FIG. 8A shows a constant high tube current ($mA_h$) continuously applied to a radiation source (e.g., the radiation source 113). FIG. 8B shows an actual kV switching waveform correlated with the constant high mA illustrated in FIG. 8A. Although the continuous high mA discharge can be used to reduce the kV fall time so as to increase spectral energy separation capability, the high mA may cause a high scan dose. The high scan dose may harm the subject's health. The balance between the mA and the scan dose should be taken into consideration.

Figures 9A, 9B:
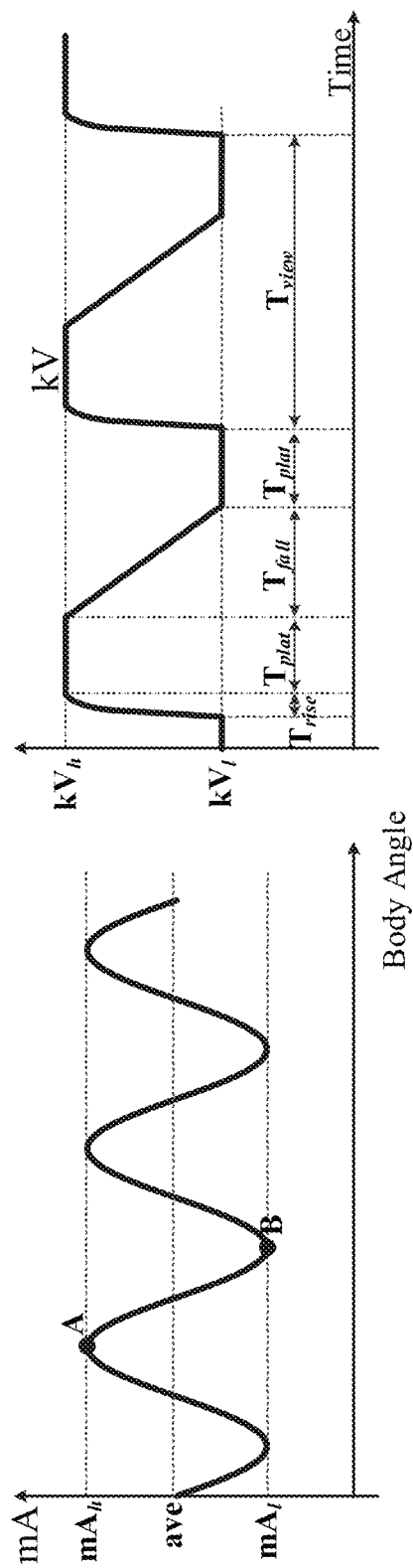
FIG. 9A is a schematic diagram illustrating an exemplary sine tube current (mV) switching waveform.
FIG. 9B is a schematic diagram illustrating an actual kV switching waveform correlated with the sine mA switching waveform of FIG. 9A.

In existing energy imaging, an mA modulation technique is widely used to reduce the scan dose, referring to FIG. 9A and FIG. 9B. FIG. 9A shows a sine mA switching waveform for the mA modulation, and FIG. 9B shows an actual kV switching waveform correlated with the sine mA switching waveform of FIG. 9A. In this situation, the mA will vary with an oval-shape human body to maintain a constant signal-noise-ratio (SNR). As described in connection with FIG. 7D, the kV fall time may be determined by the mA. For example, if the mA is at a high mA (e.g., $mA_h$), the kV fall time will become relatively short. As another example, if the mA is at a low mA (e.g., $mA_l$), the kV fall time will become relatively long. When different mAs are applied, the kV fall times may become different, accordingly. If the inverter is still shut down to achieve the shortest kV fall time during the kV fall time, then the kV fall time at the low mA (thin body path) must be much longer than that of the high mA (thick body path). In some cases, when the mA is frequently switched according to the sine mA switching waveform, which may cause a disorder of the corresponding kV switching waveform and low energy spectra separation capacity, and further a poor image quality for a scanning image. But for the energy imaging based on the fast kV switching, the kV switching waveform may need to be constant in the whole scan to avoid energy disturbance. Thus, the inverter needs to be turned on during the kV fall time. In this case, the kV fall speed at high mA may be decreased so as to for the kV switching waveform to obtain a constant kV fall time at the whole mA range, i.e., both the kV fall speed at high mA and the kV fall speed at low mA. The decrease of the fall speed will lead to increasing the kV fall time. As a result, the total scan time and scan dose may be increased greatly, counteracting the dose reduction caused by the mA modulation.

Merely by way of example, assuming that the equivalent capacitance of the HVG is 1 nF (i.e., $C_{hv}$=1 nF), both the high energy voltage plateau duration and the low energy voltage plateau duration are 100 us (i.e., $T_{plat}$=100 us), the maximum tube current is 600 mA (i.e., $mA_h$=600 mA), the minimum tube current is 200 mA (i.e., $mA_l$=200 mA), the average tube current is 400 mA (i.e., $mA_{ave}$=400 mA), the kV rise time is 100 us (i.e., $T_{rise}$=100 us), and the number of scan projections (or view counts) per round is 1000. In one energy imaging scan mode, as described in connection with FIGS. 8A-8B, if it uses a constant high mA to scan, such as 600 mA constant large mA scan, the kV fall time from 140 kV to 80 kV will be $T_{fall\_600\ mA}$=100 us, so the total scan time per round $T_s$=1000×($T_{rise}$+$T_{plat}$+$T_{plat}$+$T_{fall\_600\ mA}$)=0.4 s, which corresponds to scan dose of 240 mAs. In other energy imaging scan mode, as described in connection with FIGS. 9A-9B, if it uses the sine mA switching waveform to scan, the kV fall time will be determined by the minimum $mA_l$ (i.e., 200 mA), leading to a fall time of $T_{fall\_200\ mA}$, that is, 300 us. A total scan time per round, that is, $T_s$=1000× ($T_{rise}$+$T_{plat}$+$T_{plat}$+$T_{fall\_200\ mA}$)=0.65, which also corresponds to scan dose of 240 mAs. By comparing the two results of the two energy imaging scan modes, it is found that the two conventional mA modulation techniques can not effectively reduce the total scan dose in the dual energy imaging based on fast kV switching. Therefore, it is desirable to develop an efficient technology to achieve the dose reduction in the dual energy imaging based on fast kV switching.

Figure 5:
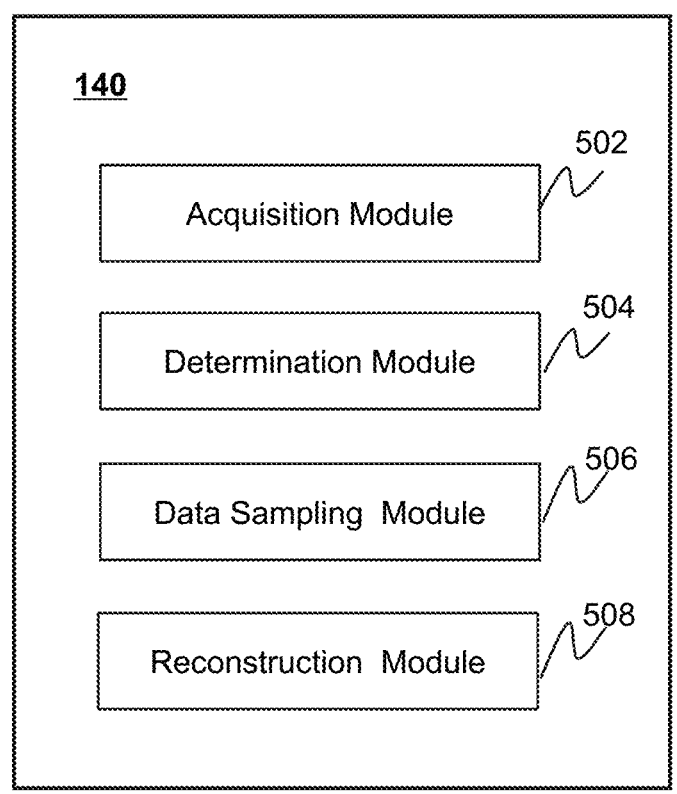
FIG. 5 is a schematic diagram illustrating an exemplary processing device according to some embodiments of the present disclosure.

FIG. 5 is a schematic diagram illustrating an exemplary processing device according to some embodiments of the present disclosure. As illustrated in FIG. 5, the processing device 140 may include an acquisition module 502, a determination module 504, a data sampling module 506, and a reconstruction module 508. At least a portion of the processing device 140 may be implemented on the computing device 300 as illustrated in FIG. 3 or the mobile device 400 as illustrated in FIG. 4.

The acquisition module 502 may be configured to acquire a tube voltage (kV) switching waveform of a radiation source (e.g., the radiation source 113) of a medical device (e.g., the imaging device 110). The kV switching waveform may be used to characterize that the kV of the radiation source varies with a time. The kV switching waveform is composed of low and high energy kVs (e.g., $kV_h$ and $kV_l$). The kV switching waveform indicates an alternation between $kV_h$ and $kV_l$ during the time duration corresponding to a plurality of views. According to the alternation between $kV_h$ and $kV_l$, the corresponding kV (e.g., $kV_h$ or $kV_l$) may be applied to the radiation source. In dual energy imaging procedure, a plurality of alternations between $kV_h$ and $kV_l$ may be performed. In some embodiments, the kV switching waveform may include periodic four kV switching stages, such as, a low energy voltage plateau duration, a rising edge, a high energy voltage plateau duration and a falling edge. The four kV switching stages may be repeated periodically.

The determination module 504 may be configured to determine a tube current (mA) switching period (also referred to as "mA switching waveform") based on the acquired kV switching waveform. The mA switching period may be indicative of an on-off state of the mA applied to the radiation source. The mA may be allowed to switch on/off according to the mA switching period. The on-off state of the mA may be indicated by an on-stage of the mA switching period and/or an off-stage of the mA switching period. If the mA is within the on-stage of the mA switching period, the mA needs be switched on. If the mA is within the off-stage of the mA switching period, the mA needs be switched off. In some embodiments, if the mA is switched on, cathode filament(s) may emit an electron beam so as to form X-rays. In some embodiments, if the mA is switched off, the electron emission of the cathode filament may be stopped. In some embodiments, the determination module 504 may determine that the mA is within the on-stage of the mA switching period in response to occurrence of the falling edge of the kV represented in the kV switching waveform. The on-stage of mA includes the time duration of the falling edge of the kV such that the high rated mA stayed at the on-stage may reduce the kV fall time. In some embodiments, the determination module 504 may determine an off-stage of mA followed by an on-stage of mA. The on-stage of mA and the off-stage of mA alternate in the mA switching period. More descriptions of the determination of on-stages and off-stages of mA may be found elsewhere in the present disclosure, e.g., FIG. 6, FIGS. 10A-FIG. 15, and the descriptions thereof.

The determination module 504 may be configured to determine a sampling period correlated with the mA switching period. Projection data may be collected based on the sampling period. In some embodiments, the sampling period and the mA switching period need to coordinate with each other so as to achieve a good energy spectra separation. The determination module 504 may determine, based on an on-off state of the mA, a sampling on-stage and a sampling off-stage, respectively. In some embodiments, the sampling on-stage may include at least part of the time duration corresponding to the on-stage of mA. The determination module 504 may determine a sampling off-stage followed by a sampling on-stage. The sampling on-stage and the sampling off-stage alternate in the mA switching period. More descriptions of the determination of sampling on-stages and sampling off-stages may be found elsewhere in the present disclosure, e.g., FIG. 6, FIGS. 10A-FIG. 15, and the descriptions thereof.

The data sampling module 506 may be configured to acquire projection data according to the sampling period. For example, the projection data corresponding to the sampling on-stage may be collected. The projection data may include first projection data under the high energy kV and second projection data under the low energy kV. The data sampling module 506 may collect the projection data corresponding to the sampling on-stage. The acquired data may be stored in a storage device (e.g., the storage device 150).

The reconstruction module 508 may be configured to reconstruct an imaging based on the acquired projection data. The reconstruction module 508 may reconstruct the image using a reconstruction algorithm. Exemplary reconstruction algorithms may include but are not limited to an algebraic reconstruction technique (ART), a simultaneous algebra reconstruction technique (SART), a filtered back projection (FBP) technique, a Feldkamp-Davis-Kress (FDK) reconstruction technique, an iterative reconstruction technique, a convolution back projection (CBP) technique, a Fourier back projection technique, or the like, or any combination thereof.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, the processing device 140 may further include a storage module (not shown in FIG. 5). The storage module may be configured to store data generated during any process performed by any component of in the processing device 140. As another example, each of components of the processing device 140 may include a storage device. Additionally or alternatively, the components of the processing device 140 may share a common storage device.

Figure 6:
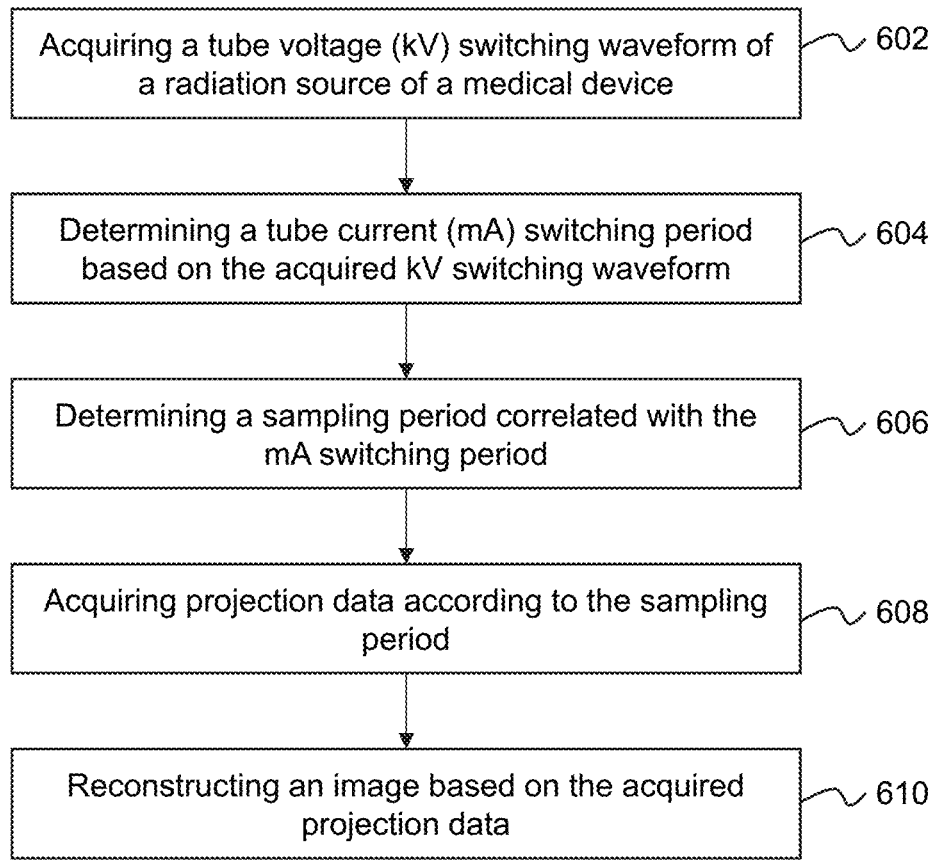
FIG. 6 is a flowchart illustrating an exemplary energy imaging process according to some embodiments of the present disclosure.

FIG. 6 is a flowchart illustrating an exemplary energy imaging process according to some embodiments of the present disclosure. In some embodiments, one or more operations of process 600 illustrated in FIG. 6 may be implemented in the imaging system 100 illustrated in FIG. 1. For example, the process 600 may be stored in a storage medium (e.g., the storage device 150, and/or the storage 320) of the imaging system 100 in the form of instructions, and invoked and/or executed by the processing device 140 (e.g., the processor 310 of the computing device 300 as illustrated in FIG. 3, the CPU 440 of the mobile device 400 as illustrated in FIG. 4, or one or more modules/units/blocks of the processing device 140 illustrated in FIG. 5). The operations of the illustrated process presented below are intended to be illustrative. In some embodiments, the process 600 may be accomplished with one or more additional operations not described, and/or without one or more of the operations discussed. Additionally, the order in which the operations of the process 600 as illustrated in FIG. 6 and described below is not intended to be limiting.

In 602, the processing device 140 (e.g., the acquisition module 502 of the processing device 140) may acquire a tube voltage (kV) switching waveform of a radiation source (e.g., the radiation source 113) of a medical device (e.g., the imaging device 110). The kV switching waveform may be used to characterize that the kV of the radiation source varies with a time. The kV switching waveform is composed of low and high energy kVs (e.g., $kV_h$ and $kV_l$). The kV switching waveform indicates an alternation between $kV_h$ and $kV_l$ during the time duration corresponding to a plurality of views. According to the alternation between $kV_h$ and $kV_l$, the corresponding kV (e.g., $kV_h$ or $kV_l$) may be applied to the radiation source. In dual energy imaging procedure, a plurality of alternations between $kV_h$ and $kV_l$ may be performed.

As described in connection with FIG. 7A and FIG. 7B, for a kV control of the radiation source, it is difficult to achieve the ideal kV switching waveform (e.g., square kV pulses shown in FIG. 7A) due to limitations of physical conditions (e.g., the limitations of the HVG and the loss in the system). As shown in FIG. 7B, the actual kV switching waveform can not include perfect square pulses as the ideal kV switching waveform of FIG. 7A. The actual kV switching waveform may include periodic four kV switching stages, such as, a low energy voltage plateau duration, a rising edge, a high energy voltage plateau duration and a falling edge. The four kV switching stages may be repeated periodically. The low energy voltage plateau duration corresponds to the time duration when the low energy kV ($kV_l$) lasts. The rising edge corresponds to the kV rise time when $kV_l$ rises to $kV_h$. The high energy voltage plateau duration corresponds to the time duration when the high energy kV ($kV_h$) lasts. The falling edge corresponds to the kV fall time when $kV_h$ falls to $kV_l$.

In some embodiments, the processing device 140 may obtain a designed input kV switching waveform from a storage device (e.g., the storage device 150). For example, the designed input kV switching waveform may be an ideal kV switching waveform composed of a plurality of square kV pulses, as illustrated in FIG. 7A. The designed input kV switching waveform may be input to the imaging device 110 to direct the kV switching. In some embodiments, the processing device 140 may acquire an actual kV switching waveform associated with the designed input kV switching waveform. In some embodiments, the actual kV switching waveform may be used to determine an mA switching period (e.g., operation 602). As another example, the designed input kV switching waveform may be a waveform similar to an actual kV switching waveform illustrated in FIG. 7B. The designed input waveform may include the periodic four kV switching stages, such as, the low energy voltage plateau duration, the rising edge, the high energy voltage plateau duration and the falling edge. Merely by way of example, the acquired kV switching waveform may include one of the kV switching waveforms of FIG. 10A-FIG. 15.

In 604, the processing device 140 (e.g., the determination module 504 of the processing device 140) may determine a tube current (mA) switching period (also referred to as "mA switching waveform") based on the acquired tube voltage (kV) switching waveform. The mA switching period may be indicative of an on-off state of the mA applied to the radiation source. The mA may be allowed to switch on/off according to the mA switching period. The on-off state of the mA may be indicated by an on-stage of the mA switching period and/or an off-stage of the mA switching period. If the mA is within the on-stage of the mA switching period, the mA needs be switched on. If the mA is within the off-stage of the mA switching period, the mA needs be switched off. In some embodiments, if the mA is switched on, cathode filament(s) may emit an electron beam so as to form X-rays. In some embodiments, if the mA is switched off, the electron emission of the cathode filament may be stopped.

In some embodiments, when the mA is within the on-stage, the mA may be stayed at a rated mA value. The rated mA value may be a constant mA value. If the rated mA is a relatively high mA value (e.g., 600 mA), which facilitates to reduce kV fall time. In some embodiments, when the mA is within the off-stage, the mA may be stayed at zero or about zero value, that is, there may be no mA during the time duration of the off-stage of mA and there may be almost no scan dose to be generated. In some embodiments, the mA may be periodically switched on/off with the alternation between the on-stage and the off-stage. Compared with the continuous mA discharge illustrated in FIG. 8A or FIG. 9A, the periodic mA discharge may effectively reduce the total scan dose of a whole scan.

The mA switching period may be correlated with the kV switching waveform. In some embodiments, the mA switching may affect the kV switching. The mA switching and the kV switching need coordinate with each other so as to achieve a good dual energy imaging effect. The processing device 140 may determine the suitable mA switching period according to the kV switching waveform. For example, the determination module 504 may determine on-stage(s) and off-stage(s) of the mA such that the on-stage(s) and the off-stage(s) is matched with the kV switching stage(s), such as the low energy voltage plateau duration, the rising edge, the high energy voltage plateau duration and the falling edge.

Figure 10A:
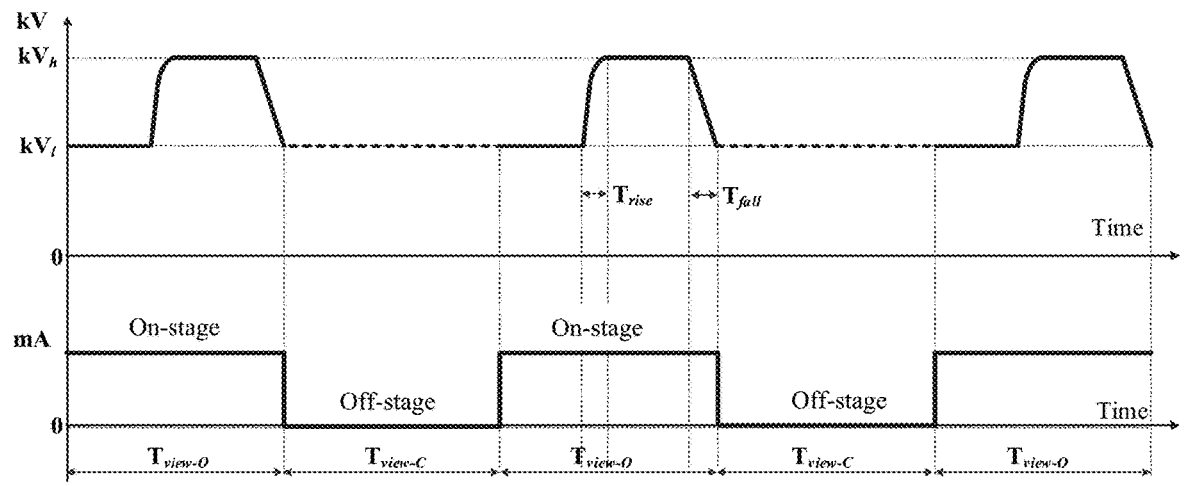
FIG. 10A is a schematic diagram illustrating a first relation between a tube voltage (kV) and a tube current (mA) applied to a radiation source according to some embodiments of the present disclosure.
Figure 10B:
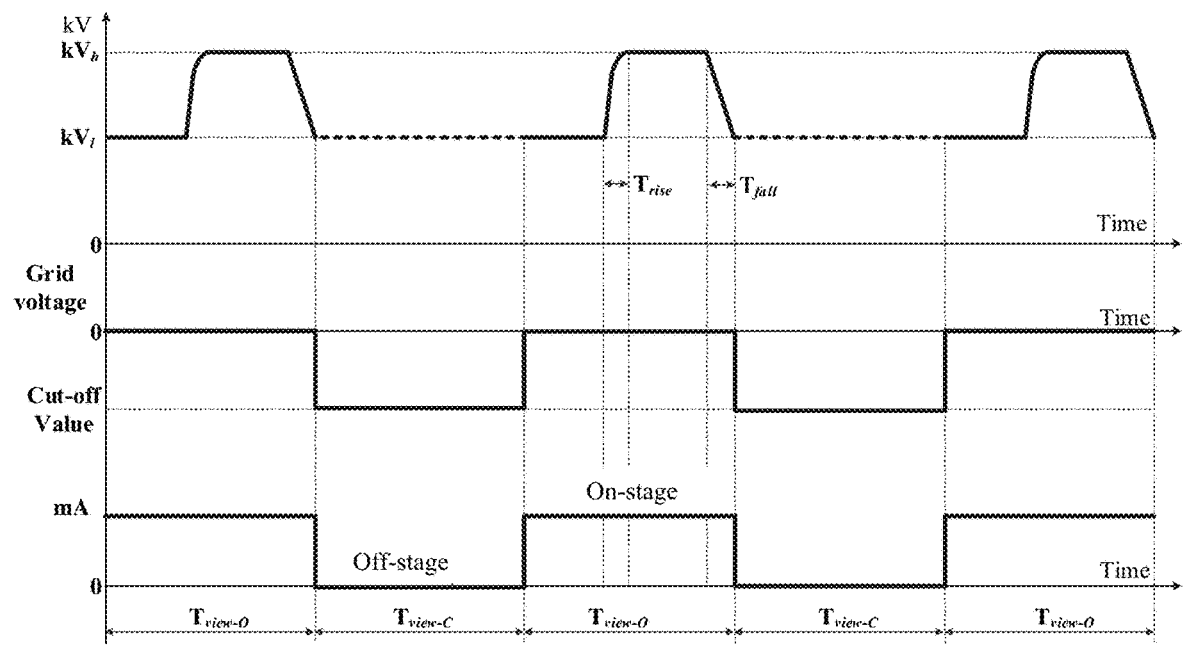
FIG. 10B is a schematic diagram illustrating an exemplary implementation sequence chart of a dual energy imaging method according to some embodiments of the present disclosure.
Figure 11:
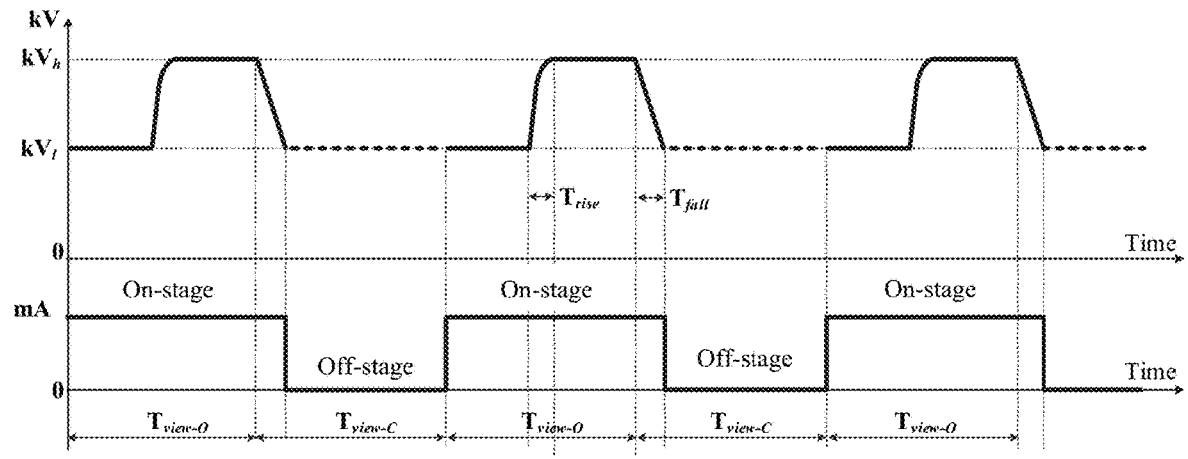
FIG. 11 is a schematic diagram illustrating a second relation between a tube voltage (kV) and a tube current (mA) applied to a radiation source according to some embodiments of the present disclosure.
Figure 12:
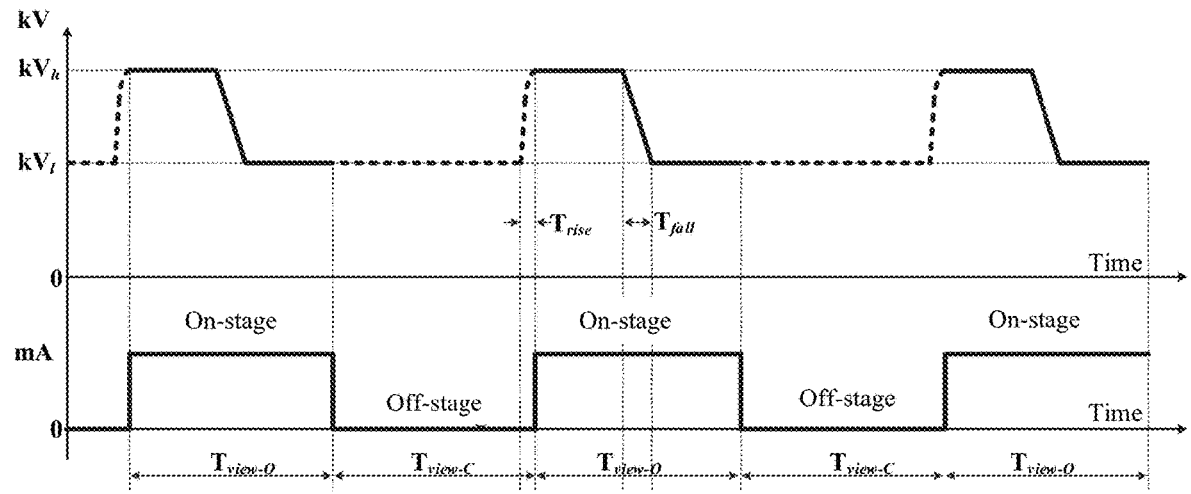
FIG. 12 is a schematic diagram illustrating a third relation between a tube voltage (kV) and a tube current (mA) applied to a radiation source according to some embodiments of the present disclosure.
Figure 13:
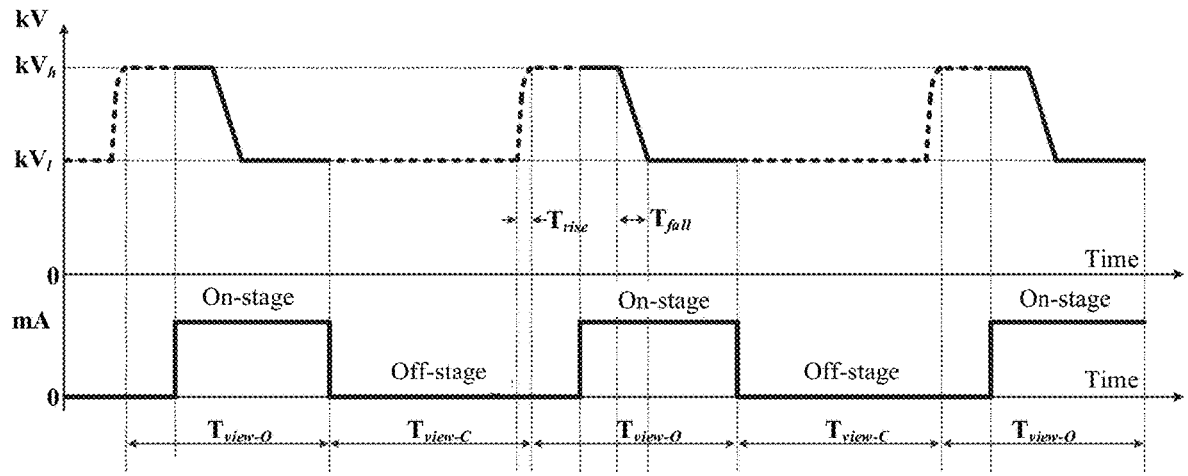
FIG. 13 is a schematic diagram illustrating a fourth relation between a tube voltage (kV) and a tube current (mA) applied to a radiation source according to some embodiments of the present disclosure.
Figure 14:
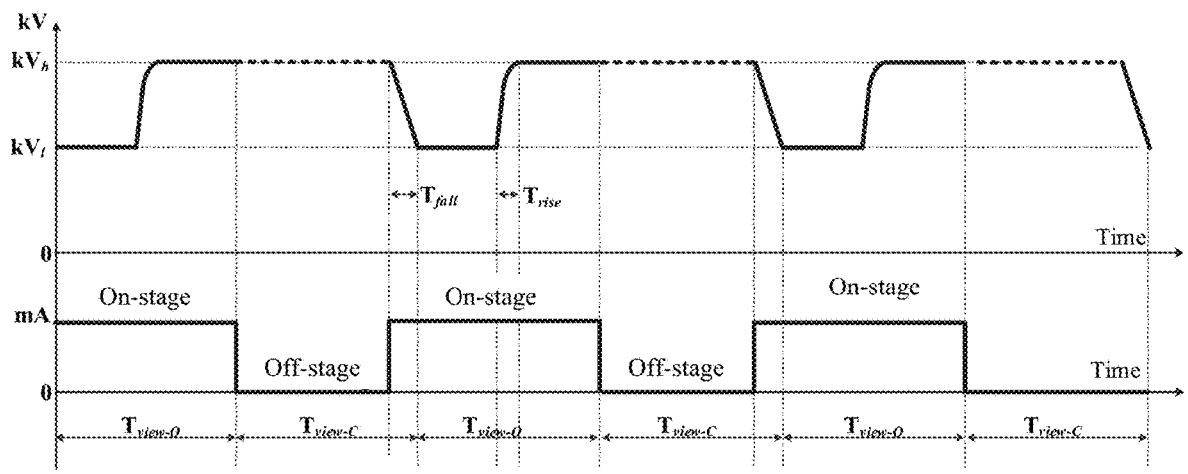
FIG. 14 is a schematic diagram illustrating a fifth relation between a tube voltage (kV) and a tube current (mA) applied to a radiation source according to some embodiments of the present disclosure.
Figure 15:
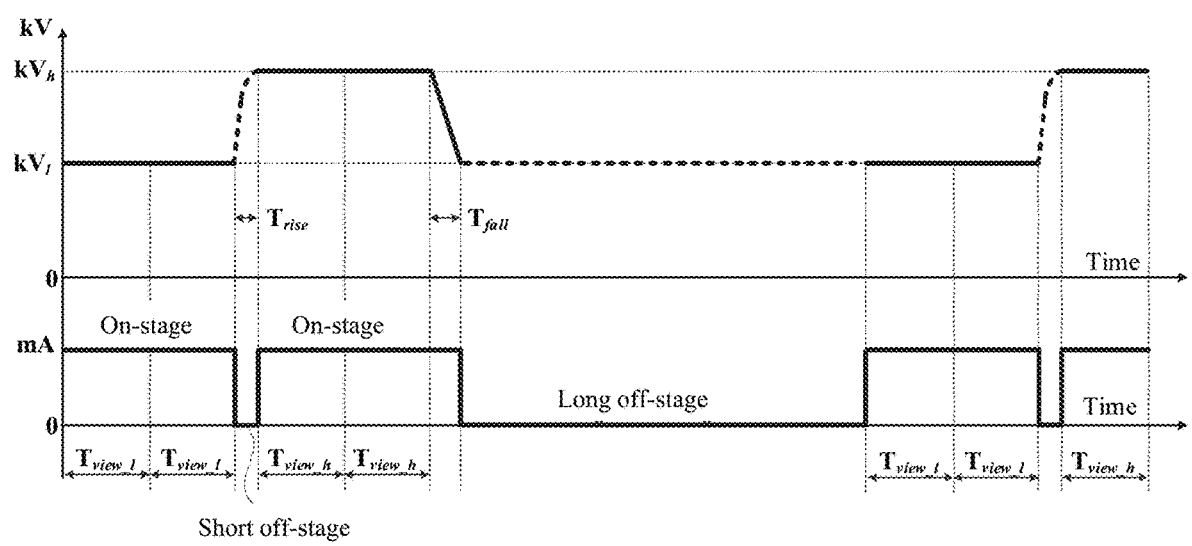
FIG. 15 is a schematic diagram illustrating a sixth relation between a tube voltage (kV) and a tube current (mA) applied to a radiation source according to some embodiments of the present disclosure.

In some embodiments, the processing device 140 may determine that the mV is within the on-stage of the mA switching period in response to occurrence of the falling edge of the kV represented in the kV switching waveform. The on-stage of mA includes the time duration of the falling edge of the kV such that the high rated mA stayed at the on-stage may reduce the kV fall time. Referring to one of FIG. 10A-FIG. 15, it is found that the on-stage of mA includes the time duration of the falling edge of the kV. As illustrated in FIG. 10A or FIG. 11, an on-stage of mA may correspond to the time duration including a portion of the low energy voltage plateau duration, the rising edge, the high energy voltage plateau duration and the falling edge, which are represented by a solid line in the kV switching waveform. As illustrated in FIG. 12, an on-stage of mA may correspond to the time duration including the high energy voltage plateau duration, the falling edge and a portion of the low energy voltage plateau duration, which are represented by a solid line in the kV switching waveform. As illustrated in FIG. 13, an on-stage of mA may correspond to the time duration including a portion of high energy voltage plateau duration, the falling edge and a portion of the low energy voltage plateau duration, which are represented by a solid line in the kV switching waveform. As illustrated in FIG. 14, an on-stage of mA may correspond to the time duration including the low energy voltage plateau duration, the rising edge and a portion of the high energy voltage plateau duration, which are represented by a solid line in the kV switching waveform. As illustrated in FIG. 15, a first on-stage of mA may correspond to the time duration including a portion of the low energy voltage plateau duration, which is represented by a solid line in the kV switching waveform. A second on-stage of mA may correspond to the time duration including the high energy voltage plateau duration and the falling edge, which are represented by a solid line in the kV switching waveform. The rising edge is between the first on-stage of mA and the second on-stage of mA.

In some embodiments, the processing device 140 may determine an off-stage of mA followed by an on-stage of mA. The on-stage of mA and the off-stage of mA alternate in the mA switching period.

As illustrated in FIG. 10A or FIG. 11, the processing device 140 may determine that the mA is within an off-stage of mA switching period in response to occurrence of kV between a first predetermined time of the low energy voltage plateau duration and a second predetermined time of the low energy voltage plateau duration. An off-stage of mA may correspond to a portion of the low energy voltage plateau duration, such as the time duration between the first predetermined time of the low energy voltage plateau duration and the second predetermined time of the low energy voltage plateau duration, which is represented by a dashed line in the kV switching waveform. The first predetermined time may be the ending point of a falling edge of kV. The second predetermined time may be a time point later than the first predetermined time. In some embodiments, a time interval between the first predetermined time and the second predetermined time may be equal to a first threshold. The first threshold may be less than or equal to the time duration of an on-stage of mA, such as the time duration of one view.

As illustrated in FIG. 12, the processing device 140 may determine that the mA is within an off-stage of the mA switching period in response to occurrence of kV between a third predetermined time of the low energy voltage plateau duration and a fourth predetermined time of the rising edge. An off-stage of mA may correspond to the time duration including a portion of the low energy voltage plateau duration and the rising edge, which are represented by a dashed line in the kV switching waveform, such as the time duration between the third predetermined time of the low energy voltage plateau duration and the fourth predetermined time of rising edge. The fourth predetermined time may be the ending point of a rising edge of kV. The third predetermined time may be a time point earlier than the fourth predetermined time. In some embodiments, a time interval between the third predetermined time and the fourth predetermined time may be equal to a second threshold. The second threshold may be less than or equal to the time duration of an on-stage of mA, such as the time duration of one view.

As illustrated in FIG. 13, the processing device 140 may determine that the mA is within an off-stage of the mA switching period in response to occurrence of kV between a fifth predetermined time of the low energy voltage plateau duration and a sixth predetermined time of the high energy voltage plateau duration. An off-stage of mA may correspond to the time duration including a portion of the low energy voltage plateau duration, the rising edge and a portion of the high energy voltage plateau duration, which are represented by a dashed line in the kV switching waveform, such as the time duration between the fifth predetermined time of the low energy voltage plateau duration and the sixth predetermined time of the high energy voltage plateau duration. The fifth predetermined time may be a specified time point of the low energy voltage plateau duration. The sixth predetermined time may be another specified time point of the high energy voltage plateau duration. The sixth predetermined time is later than the fifth predetermined time. In some embodiments, a time interval between the fifth predetermined time and the sixth predetermined time may be equal to a third threshold. The third threshold may be greater than or equal to the time duration of an on-stage of mA, such as the time duration of one view.

As illustrated in FIG. 14, the processing device 140 may determine that the mA is within an off-stage of the mA switching period in response to occurrence of kV between a seventh predetermined time of the high energy voltage plateau duration and an eighth predetermined time of the high energy voltage plateau duration. An off-stage of mA may correspond to the time duration including a portion of the high energy voltage plateau duration, which is represented by a dashed line in the kV switching waveform, such as the time duration between the seventh predetermined time of the high energy voltage plateau duration and the eighth predetermined time of the high energy voltage plateau duration. The eighth predetermined time may be the starting point of a falling edge of kV. The seventh predetermined time is a time point earlier than the eighth predetermined time. In some embodiments, a time interval between the seventh predetermined time and the eighth predetermined time may be equal to a fourth threshold. The fourth threshold may be less than the high energy voltage plateau duration.

As illustrated in FIG. 15, the processing device 140 may determine that the mA is within a short off-stage of the mA switching period in response to occurrence of kV between a ninth predetermined time and a tenth predetermined time of the rising edge, and a long off-stage of the mA switching period in response to occurrence of kV between a eleventh predetermined time of the low energy voltage plateau duration and a twelfth predetermined time of the low energy voltage plateau duration. A short off-stage of mA may correspond to the time duration including the rising edge, which is represented by a dashed line in the kV switching waveform, such as the time duration between the ninth predetermined time and the tenth predetermined time of the rising edge. The ninth predetermined time may be the starting point of the rising edge of kV. The tenth predetermined time may be the ending point of the rising edge of kV. A long off-stage of mA may correspond to a portion of the low energy voltage plateau duration which is represented by a dashed line in the kV switching waveform, such as the time duration between the eleventh predetermined time of the low energy voltage plateau duration and the twelfth predetermined time of the low energy voltage plateau duration. The eleventh predetermined time may be the ending point of the falling edge of kV. The twelfth predetermined time may be a time point later than the eleventh predetermined time. In some embodiments, a time interval between the eleventh predetermined time and the twelfth predetermined time may be equal to a fifth threshold. The fifth threshold may be less than the low energy voltage plateau duration.

In some embodiments, the switching of mA may be controlled by a grid voltage of a grid electrode (e.g., the grid electrode illustrated in FIG. 2). For example, if the grid voltage is switched to a cut-off voltage (e.g., a negative voltage value), the mA may be switched off accordingly. There may be no mA to be discharged during the off-stage of mA. As another example, if the grid voltage is switched to zero or about zero value, the mA may be switched on. It should be noted that the means for controlling the on-off state of the mA may be not intended to be limiting, and any suitable means may be applied to the control of the on-off state of the mA.

In 606, the processing device 140 (e.g., the determination module 504 of the processing device 140) may determine a sampling period correlated with the mA switching period. Projection data may be collected based on the sampling period. In some embodiments, the sampling period and the mA switching period need coordinate with each other so as to achieve a good energy spectra separation.

Exemplary sampling methods for the projection data may include a complete sampling method and an undersampling method. The complete sampling method may include collecting all projection data occurred during the sampling period. The undersampling method may include collecting part of the projection data occurred during the sampling period. The collected part of the projection data may be referred as sparse data as well. In some embodiments, the typical undersampling may be adopted for the dual energy imaging. The sampling period may include sampling on-stage(s) and sampling off-stage(s). The projection data corresponding to the sampling on-stage may be allowed to collect. The projection data corresponding to the sampling off-stage may not be allowed to collect.

In some embodiments, the processing device 140 may determine the sampling period according to the mA switching period. Specifically, the processing device 140 may determine, based on an on-off state of the mA, a sampling on-stage and a sampling off-stage, respectively. In some embodiments, the sampling on-stage may include at least part of the time duration corresponding to the on-stage of mA. In one embodiment, as illustrated in FIG. 10A, one sampling on-stage (e.g., $T_{view-O}$) corresponds to one on-stage of mA. In another embodiment, as illustrated in FIG. 11, one sampling on-stage (e.g., $T_{view-O}$) corresponds to the time duration including a portion of the low energy voltage plateau duration (e.g., the low energy voltage plateau duration represented by a solid line in the kV switching waveform), the rising edge, and the high energy voltage plateau duration. The sampling on-stage includes part of the time duration corresponding to the on-stage of mA. In another embodiment, as illustrated in FIG. 12, one sampling on-stage (e.g., $T_{view-O}$) corresponds to one on-stage of mA. In another embodiment, as illustrated in FIG. 13, one sampling on-stage (e.g., $T_{view-O}$) corresponds to the time duration including an on-stage of mA and part of an off-stage of mA. In another embodiments, as illustrated in FIG. 14, one sampling on-stage (e.g., $T_{view-O}$) corresponds to one on-stage of mA. In another embodiments, as illustrated in FIG. 15, one sampling on-stage corresponds to the on-stage of mA, for example, two consecutive $T_{view-l}$ and/or two consecutive $T_{view-h}$. $T_{view-l}$ represents the time duration of a low energy projection, and $T_{view-h}$ represents the time duration of a high energy projection.

In some embodiments, the processing device 140 may determine a sampling off-stage followed by a sampling on-stage. The sampling on-stage and the sampling off-stage alternate in the mA switching period.

As illustrated in FIG. 10A, the processing device 140 may determine that one sampling off-stage is between a thirteenth predetermined time of the low energy voltage plateau duration and a fourteenth predetermined time of the low energy voltage plateau duration. The sampling off-stage starts at the thirteenth predetermined time of the low energy voltage plateau duration and ends at the fourteenth predetermined time of the low energy voltage plateau duration, such as the low energy voltage plateau duration represented by a dashed line in the kV switching waveform. The sampling off-stage corresponds to the off-stage of mA. The thirteenth predetermined time may be the same as the first predetermined time, and the fourteenth predetermined time may be the same as the second predetermined time. For example, the thirteenth predetermined time may be the ending point of a falling edge of kV. The fourteenth predetermined time may be a time point later than the thirteenth predetermined time. The time interval between the thirteenth predetermined time and the fourteenth predetermined time may be equal to the first threshold.

As illustrated in FIG. 11, the processing device 140 may determine that one sampling off-stage is between a fifteenth predetermined time of the low energy voltage plateau duration and a sixteenth predetermined time of the low energy voltage plateau duration. The sampling off-stage starts at the fifteenth predetermined time of the falling edge and ends at the sixteenth predetermined time of the low energy voltage plateau duration. The fifteenth predetermined time may be the starting point of the falling edge and the sixteenth predetermined time may be the same as the second predetermined time.

As illustrated in FIG. 12, the processing device 140 may determine that one sampling off-stage is between a seventeenth predetermined time of the low energy voltage plateau and an eighteenth predetermined time of the rising edge. The sampling off-stage starts at the seventeenth predetermined time of the low energy voltage plateau duration and ends at the eighteenth predetermined time of the rising edge, such as the low energy voltage plateau duration and the kV rise time represented by a dashed line in the kV switching waveform. The sampling off-stage corresponds to the off-stage of mA. The seventeenth predetermined time may be the same as the third predetermined time, and the eighteenth predetermined time may be the same as the fourth predetermined time. For example, the eighteenth predetermined time may be the ending point of a rising edge of kV, and the seventeenth predetermined time may be a time point earlier than the fourth predetermined time. The time interval between the seventeenth predetermined time and the eighteenth predetermined time may be equal to the second threshold.

As illustrated in FIG. 13, the processing device 140 may determine that one sampling off-stage is between a nineteenth predetermined time of the high energy voltage plateau duration and a twentieth predetermined time of the falling edge. The sampling off-stage starts at the nineteenth predetermined time of the high energy voltage plateau duration and ends at the twentieth predetermined time of the falling edge, such as the high energy voltage plateau duration represented by a dashed line in the kV switching waveform. The nineteenth predetermined time may be the same as the fifth predetermined time, and the twentieth predetermined time may be the ending point of the falling edge.

As illustrated in FIG. 14, the processing device 140 may determine that one sampling off-stage is between a twenty-first predetermined time of the high energy voltage plateau duration and a twenty-second predetermined time of the falling edge. As shown in FIG. 14, one sampling off-stage starts at the twenty-first predetermined time of the high energy voltage plateau duration and ends at the twenty-second predetermined time of the falling edge, such as the high energy voltage plateau duration represented by a dashed line in the kV switching waveform. The twenty-first predetermined time may be the same as the seventh predetermined time, and the twenty-second predetermined time may be the ending point of the falling edge.

As illustrated in FIG. 15, the processing device 140 may determine that one short sampling off-stage is between a twenty-third predetermined time of the rising edge and a twenty-fourth predetermined time of the rising edge, and a long sampling off-stage is between a twenty-fifth predetermined time of the falling edge and a twenty-sixth predetermined time of the low energy voltage plateau duration. The short sampling off-stage starts at the twenty-third predetermined time of the rising edge and ends at the twenty-fourth predetermined time of the rising edge. The long sampling off-stage starts at the twenty-fifth predetermined time of the falling edge and ends at the twenty-sixth predetermined time of the low energy voltage plateau duration. The short sampling off-stage corresponds to the short off-stage of mA and the long sampling off-stage corresponds to the long off-stage of mA. The twenty-third predetermined time may be the same as the ninth predetermined time. The twenty-fourth predetermined time may be the same as the tenth predetermined time. The twenty-fifth predetermined time may be the same as the eleventh predetermined time. The twenty-sixth predetermined time may be the same as the twelfth predetermined time.

In some embodiments, the time duration of the sampling on-stage may be an integral number of the time duration of the sampling off-stage, which may ensure that a rotation angle of the radiation source is at the same angle whatever the mA is within the on-stage or the off-stage.

In 608, the processing device 140 (e.g., the data sampling module 506 of the processing device 140) may acquire projection data according to the sampling period. For example, the projection data corresponding to the sampling on-stage may be collected. The projection data may include first projection data under the high energy kV and second projection data under the low energy kV. The data sampling module 506 may collect the projection data corresponding to the sampling on-stage. The acquired data may be stored in a storage device (e.g., the storage device 150).

In some embodiments, all the projection data corresponding to the sampling period may be collected. Such collected projection data may be deemed as complete sampled data. The data sampling module 506 may collect the complete sampled data. The acquired data may be stored in a storage device (e.g., the storage device 150). In some embodiments, the sampling period may include sampling on-stage(s) and sampling off-stage(s). The projection data corresponding to the sampling on-stage may be collected. Such collected projection data may be deemed as undersampled data. In some embodiments, the projection data may include first projection data under the high energy kV and second projection data under the low energy kV. The data sampling module 506 may collect the projection data corresponding to the sampling on-stage. The acquired data may be stored in a storage device (e.g., the storage device 150).

In 610, the processing device 140 (e.g., the reconstruction module 508 of the processing device 140) may reconstruct an imaging based on the acquired projection data. In some embodiments, the processing device 140 may reconstruct the image based on the complete sampled projection data. In some embodiments, the processing device 140 may reconstruct the image based on the undersampled projection data. For example, the reconstruction module 508 may generate, based on the undersampled projection data, compensation data using an interpolation algorithm. Exemplary interpolation algorithms include a nearest neighbor interpolation, a linear interpolation, a cubic interpolation, or the like, or any combination thereof. The processing device 140 may reconstruct the image based on the undersampled data and the compensation data. As another example, the processing device 140 may directly reconstruct the image based on the undersampled projection data.

In some embodiments, the processing device 140 may reconstruct the image using a reconstruction algorithm. Exemplary reconstruction algorithms may include but are not limited to an algebraic reconstruction technique (ART), a simultaneous algebra reconstruction technique (SART), a filtered back projection (FBP) technique, a Feldkamp-Davis-Kress (FDK) reconstruction technique, an iterative reconstruction technique, a convolution back projection (CBP) technique, a Fourier back projection technique, or the like, or any combination thereof.

In some embodiments, if the kV falling edge occurs, the inverter of the HVG may be turned off. In some embodiments, if the kV rising edge occurs, the inverter of the HVG may be turned on. In some embodiments, if the high energy voltage plateau duration or the low energy voltage plateau duration, in sync with the occurrence of the on-stage of mA, occurs, the inverter may be turned on. In some embodiments, if the high energy voltage plateau duration and the low energy voltage plateau duration, in sync with the occurrence of the off-stage of the mA, occurs, the inverter may be turned on or turned off.

During the scan, the actual kV switching waveform may not be composed of perfect square kV pulses of FIG. 7A due to limitations of the HVG and loss in the system. To make the actual kV switching waveform close to the ideal kV switching waveform, the kV fall time and/or the kV rise time should be limited to a relatively short time. The fast kV switching is important for the dual energy imaging. In some embodiments, during the kV fall time, a constant high mA may be applied to the radiation source so as to reduce the kV fall time and improve the spectral energy separation. Besides, the mA may be periodically switched on/off according to the determined mA switching period. The periodic mA discharge may effectively reduce the total scan dose of a whole scan.

Example 1

FIG. 10A shows a first relation between a tube voltage (kV) and a tube current (mA) applied to a radiation source according to some embodiments of the present disclosure. As illustrated in FIG. 10A, one on-stage of mA may correspond to the time duration including a portion of the low energy voltage plateau duration, the rising edge, the high energy voltage plateau duration and the falling edge, which are represented by a solid line in the kV switching waveform. One off-stage may correspond to a portion of the low energy voltage plateau duration, which is represented by a dashed line in the kV switching waveform. The on-stage of mA and the off-stage of mA may alternate during the dual energy imaging. In some embodiments, the sampling period may be correlated with the mA switching period. The sampling period may include sampling on-stage(s) (e.g., $T_{view-O}$ representing the time duration of one sampling on-stage) and sampling off-stage(s) ($T_{view-C}$ representing the time duration of one sampling off-stage). Referring to FIG. 10A, one sampling on-stage may correspond to the on-stage of mA, and one sampling off-stage may correspond to the off-stage of mA. According to the kV switching waveform and the mA switching period illustrated in FIG. 10A, the dual energy imaging may be performed.

According to the waveforms of kV and mA illustrated in FIG. 10A, during the mA is within the on-stage, the mA may be set as a rated mA value. The rated mA value may be designated as a constant high mA value (e.g., 600 mA) in order to reduce kV fall time. While the $kV_h$ falls to the $kV_l$, the high rated mA may be maintained in order to reduce the kV fall time. The actual kV switching waveform may close to the ideal kV switching waveform. Thereby the spectral energy separation may be improved. During the mA is within the off-stage, the mA may be set as zero value or about zero value, that is, there may be no mA, whereby there may be no scan dose to be generated during the off-stage of mA. The scan dose of a whole scan may be effectively reduced.

In some embodiments, an on-off state of mA may be controlled by a grid voltage of a grid electrode (e.g., the grid electrode illustrated in FIG. 2). FIG. 10B shows an exemplary implementation sequence chart of the dual energy imaging method according to some embodiments of the present disclosure. As illustrated in FIG. 10B, the switching of mA is synchronized with the switching of the grid voltage. The dual energy imaging may be performed by synchronously switching kV, mA and the grid voltage illustrated in FIG. 10B. Merely for illustration, the processing device 140 may cause the HVG to apply the kV to the radiation source 113 according to the kV switching waveform. The processing device 140 may cause the switching of grid voltage to switch on/off the mA. The switching period of the grid voltage may be synchronized with the mA switching period. For example, during the on-stage of mA, the processing device 140 may cause the grid voltage of the grid electrode to be at zero or about zero, which may allow the electron emission of the cathode filament so that the mA may be maintained at the rated mA value (e.g., 600 mA). As another example, during the off-stage of mA, the processing device 140 may cause the grid voltage of the grid electrode to be a cut-off voltage. The cut-off voltage may be designated as a negative voltage value. Thus, the electron emission of the cathode filament may be stopped due to the limitation of the negative grid voltage. The mA may be switched off, accordingly, and there is no mA. During the sampling on-stages ($T_{view-O}$), the projection data may be collected. During the sampling off-stages, the projection data may not need to be collected. The processing device 140 may cause the imaging device 110 to repeat the synchronous switching process for the kV and the mA illustrated in FIG. 10B until the dural energy imaging is completed. By adopting the synchronous switching process of FIG. 10B, the scan dose caused by the dual energy imaging may be effectively reduced. That is good for the subject's health. Given that the rated mA is 600 mA, the total scan time per round is 0.4 s, the scan dose per scan round could be reduced from 240 mAs to 120 mAs.

Example 2

FIG. 11 shows a second relation between a tube voltage (kV) and a tube current (mA) applied to a radiation source according to some embodiments of the present disclosure. The kV switching waveform and the mA switching period illustrated in FIG. 11 may be the same as or similar to the kV switching waveform and the mA switching period illustrated in FIG. 10A or FIG. 10B. However, the sampling period correlated with the mA switching period illustrated in FIG. 11 is different than the sampling period correlated with the mA switching period illustrated in FIG. 10. As illustrated in FIG. 11, one on-stage of mA may correspond to the time duration including a portion of the low energy voltage plateau duration, the rising edge, the high energy voltage plateau duration and the falling edge, which are represented by a solid line in the kV switching waveform. One off-stage may correspond to a portion of the low energy voltage plateau duration, which is represented by a dashed line in the kV switching waveform. The one-stage of mA and the off-stage of mA may alternate during the dual energy imaging. One sampling on-stage (e.g., $T_{view-O}$) may correspond to the time duration including a portion of the low energy voltage plateau duration (e.g., the low energy voltage plateau duration represented by a solid line in the kV switching waveform), the rising edge, and the high energy voltage plateau duration. The sampling on-stage includes part of the time duration corresponding to the on-stage of mA, excluding the time duration corresponding to the falling edge. A sampling off-stage is followed by the sampling on-stage. One sampling off-stage (e.g., $T_{view-C}$) may correspond to the time duration including the falling edge and the off-stage of mA. According to the kV switching waveform and the mA switching period illustrated in FIG. 11, the dual energy imaging may be performed.

As described in connection with FIG. 10B, the grid voltage may be introduced to switch on/off mA as well. The switching of mA is synchronized with the switching of the grid voltage. The dual energy imaging may be performed by synchronously switching kV, mA and the grid voltage illustrated in FIG. 11. Merely for illustration, the processing device 140 may cause the HVG to apply the kV to the radiation source 113 according to the kV switching waveform. The processing device 140 may cause the switching of grid voltage to switch on/off the mA. The switching period of the grid voltage may be synchronized with the mA switching period. For example, during the on-stage of mA, the processing device 140 may cause the grid voltage of the grid electrode to be at zero or about zero, which may allow the electron emission of the cathode filament so that the mA may be maintained at the rated mA value (e.g., 600 mA). As another example, during the off-stage of mA, the processing device 140 may cause the grid voltage of the grid electrode to be a cut-off voltage. The cut-off voltage may be designated as a negative voltage value. Thus the electron emission of the cathode filament may be stopped due to the limitation of the negative grid voltage. The mA may be switched off accordingly, and there is no mA. During the sampling on-stages ($T_{view-O}$), the projection data may be collected. During the sampling off-stages, the projection data may not need to be collected. The processing device 140 may cause the imaging device 110 to repeat the synchronous switching process for the kV and the mA illustrated in FIG. 11 until the dural energy imaging is completed. By adopting the synchronous switching process of FIG. 11, the scan dose caused by the dual energy imaging may be effectively reduced.

Compared with FIG. 10A or 10B, since the time duration corresponding to the kV falling edge is included in the sampling off-stage of FIG. 11, the projection data corresponding to the falling edge may not be collected as well. In some embodiments, the projection data corresponding to the falling edge may be set as null values. Due to the time duration of the kV rising edge is very short, most of the collected projection data may be the low energy projection data and the high energy projection data. The collected projection data may be close to the ideal projection data collected under the ideal kV switching waveform. The spectral energy separation capability may be improved. Thus an image quality of the reconstructed images using the collected projection data may be improved accordingly.

Example 3

FIG. 12 shows a third relation between a tube voltage (kV) and a tube current (mA) applied to a radiation source according to some embodiments of the present disclosure. As illustrated in FIG. 12, one on-stage of mA may correspond to the time duration including the high energy voltage plateau duration, the falling edge and a portion of the low energy voltage plateau duration, which are represented by a solid line in the kV switching waveform. One off-stage of mA may correspond to the time duration including another portion of the low energy voltage plateau duration and the rising edge, which are represented by a dashed line in the kV switching waveform. The one-stage of mA and the off-stage of mA may alternate during the dual energy imaging. In some embodiments, the sampling period may be correlated with the mA switching period. One sampling on-stage (e.g., $T_{view-O}$) may correspond to the on-stage of mA, and one sampling off-stage ($T_{view-C}$) may correspond to the off-stage of mA. According to the kV switching waveform and the mA switching period illustrated in FIG. 12, the dual energy imaging may be performed.

According to the waveforms of kV and mA illustrated in FIG. 12, during the kV switches from $kV_h$ to $kV_l$, the mA is within the on-stage, the mA may be maintained at a high rated mA (e.g., 600 mA) in order to reduce the kV fall time. Besides, during the kV switches from $kV_l$ to $kV_h$, the mA is within the off-stage, the mA may be maintained at zero or about zero value, that is, the electron emission of the cathode filament is stopped. In the situation, the inverter of the HVG may not need to supply power energy to the radiation source. The kV rise time may be effectively reduced. The actual kV switching waveform may close to the ideal kV switching waveform. Thereby the spectral energy separation may be improved. During the mA is within the off-stage, there may be no mA to be discharged, whereby there may be no scan dose to be generated during the off-stage of mA. The scan dose of a whole scan may be effectively reduced.

As described in connection with FIG. 10B, the grid voltage (not shown in FIG. 12) may be introduced to switch on/off mA as well. The switching of mA is synchronized with the switching of the grid voltage. The dual energy imaging may be performed by synchronously switching kV, mA and the grid voltage illustrated in FIG. 12. Merely for illustration, the processing device 140 may cause the HVG to apply the kV to the radiation source 113 according to the kV switching waveform. The processing device 140 may cause the switching of grid voltage to switch on/off the mA. The switching period of the grid voltage may be synchronized with the mA switching period. For example, during the on-stage of mA, the processing device 140 may cause the grid voltage of the grid electrode to be at zero or about zero, which may allow the electron emission of the cathode filament so that the mA may be maintained at the rated mA value (e.g., 600 mA). As another example, during the off-stage of mA, the processing device 140 may cause the grid voltage of the grid electrode to be a cut-off voltage. The cut-off voltage may be designated as a negative voltage value. Thus the electron emission of the cathode filament may be stopped due to the limitation of the negative grid voltage. The mA may be switched off accordingly, and there is no mA to be discharged. During the sampling on-stages ($T_{view-O}$), the projection data may be collected. During the sampling off-stages, the projection data may not need to be collected. The processing device 140 may cause the imaging device 110 to repeat the synchronous switching process for the kV and the mA illustrated in FIG. 12 until the dural energy imaging is completed. By adopting the synchronous switching process of FIG. 12, the scan dose caused by the dual energy imaging may be effectively reduced.

Since the time duration corresponding to the kV rising edge is included in the sampling off-stage of FIG. 12, the projection data corresponding to the rising edge may not be collected as well. Thus, if the time duration of the kV falling edge is very short, most of the projection data would be collected only during the low energy voltage plateau and the high energy voltage plateau. That is, the collected projection data may be close to those collected under the ideal kV switching waveform. As a result, the spectral energy separation capability may be improved. Thus, an image quality of the reconstructed images using the collected projection data may be improved accordingly.

Example 4

FIG. 13 shows a fourth relation between a tube voltage (kV) and a tube current (mA) applied to a radiation source according to some embodiments of the present disclosure. As illustrated in FIG. 13, one on-stage of mA may correspond to the time duration including a portion of the high energy voltage plateau duration, the falling edge and a portion of the low energy voltage plateau duration, which are represented by a solid line in the kV switching waveform. One off-stage of mA may correspond to the time duration including another portion of the low energy voltage plateau duration, the rising edge and another portion of the high energy voltage plateau duration, which are represented by a dashed line in the kV switching waveform. The one-stage of mA and the off-stage of mA may alternate during the dual energy imaging. In some embodiments, the sampling period may be correlated with the mA switching period. One sampling on-stage (e.g., $T_{view-O}$) may correspond to the time duration including an on-stage of mA and part of an off-stage of mA, and one sampling off-stage (e.g., $T_{view-C}$) may correspond to the time duration including another part of the off-stage of mA. According to the kV switching waveform and the mA switching period illustrated in FIG. 13, the dual energy imaging may be performed.

According to the waveforms of kV and mA illustrated in FIG. 13, even though the kV has returned to $kV_h$ for some time, the mA may be still switched off (e.g., within the off-stage of mA), thereby the electron emission of the cathode filament is stopped and there will be no mA to be discharged. Then the mA may be switched on, and the mA is within the on-stage of mA. It should be noted that the total scan dose may be determined according to, such as, kV×mA or $kV^2$. If the mA is switched off for some time during the high energy voltage plateau duration, it is obvious that the scan dose resulted from the high energy projection is reduced. Since the total energy of high energy projection is reduced, the energy balance between the high energy projection and low energy projection can be improved, whereby improving an image quality of the reconstructed image.

As described in connection with FIG. 10B, the grid voltage (not shown in FIG. 13) may be introduced to switch on/off mA as well. The switching of mA is synchronized with the switching of the grid voltage. The dual energy imaging may be performed by synchronously switching kV, mA and the grid voltage as illustrated in FIG. 13. Merely for illustration, the processing device 140 may cause the HVG to apply the kV to the radiation source 113 according to the kV switching waveform. The processing device 140 may cause the switching of grid voltage to switch on/off the mA. The switching period of the grid voltage may be synchronized with the mA switching period. For example, during the on-stage of mA, the processing device 140 may cause the grid voltage of the grid electrode to be at about zero, which may allow the electron emission of the cathode filament so that the mA may be maintained at a rated mA value. In some embodiments, the rated mA may be a relatively high mA value (e.g., 600 mA). As another example, during the off-stage of mA, the processing device 140 may cause the grid voltage of the grid electrode to be the negative cut-off voltage. Thus the electron emission of the cathode filament may be stopped due to the limitation of the negative grid voltage. The mA may be switched off accordingly, and there is no mA to be discharged. During the sampling on-stage ($T_{view-O}$), the projection data may be collected. During the sampling off-stage ($T_{view-C}$), the projection data may not need to be collected. The processing device 140 may cause the imaging device 110 to repeat the synchronous switching process for the kV and the mA illustrated in FIG. 13 until the dural energy imaging is completed. By adopting the synchronous switching process of FIG. 13, the scan dose caused by the dural energy imaging may be effectively reduced.

Example 5

FIG. 14 shows a fifth relation between a tube voltage (kV) and a tube current (mA) applied to a radiation source according to some embodiments of the present disclosure. As illustrated in FIG. 14, one on-stage of mA may correspond to the time duration including the low energy voltage plateau duration, the rising edge and a portion of the high energy voltage plateau duration, which are represented by a solid line in the kV switching waveform. One off-stage of mA may correspond to the time duration including another portion of the high energy voltage plateau duration which is represented by a dashed line in the kV switching waveform. The one-stage of mA and the off-stage of mA may alternate during the dual energy imaging. In some embodiments, the sampling period may be correlated with the mA switching period. The sampling on-stage (e.g., $T_{view-O}$) may correspond to the on-stage of mA, and the sampling off-stage ($T_{view-C}$) may correspond to the time duration including the off-stage of mA and the kV falling edge. According to the kV switching waveform and the mA switching period illustrated in FIG. 14, the dual energy imaging may be performed.

According to the waveforms of kV and mA illustrated in FIG. 14, during the mA is within the off-stage, the kV may be maintained at $kV_h$. After that the mA may be switched on and the inverter of HVG may be turned off. The mA may be switched to a relatively high rated mA value (e.g., 600 mA). The high mA may be discharged through an output capacitance of the HVG so as to quickly switch kV from $kV_h$ to $kV_l$. The kV fall time may be effectively reduced when the high mA is maintained during the kV falls. When the kV is switched to $kV_l$, the inverter of HVG may be turned on to maintain $kV_l$. The actual kV switching waveform may close to the ideal kV switching waveform. Thereby the spectral energy separation may be improved accordingly.

As described in connection with FIG. 10B, the grid voltage (not shown in FIG. 14) may be introduced to switch on/off mA. The switching of mA is synchronized with the switching of the grid voltage. The dual energy imaging may be performed by synchronously switching kV, mA and the grid voltage. Merely for illustration, the processing device 140 may cause the HVG to apply the kV to the radiation source 113 according to the kV switching waveform. The processing device 140 may cause the switching of grid voltage to switch on/off the mA. The switching period of the grid voltage may be synchronized with the mA switching period. For example, during the on-stage of mA, the processing device 140 may cause the grid voltage of the grid electrode to be at about zero, which may allow the electron emission of the cathode filament so that the mA may be maintained at a rated mA value. In some embodiments, the rated mA may be a relatively high mA value (e.g., 600 mA). As another example, during the off-stage of mA, the processing device 140 may cause the grid voltage of the grid electrode to be the negative cut-off voltage. Thus the electron emission of the cathode filament may be stopped due to the limitation of the negative grid voltage. The mA may be switched off accordingly, and there is no mA. During the sampling on-stage (e.g., $T_{view-O}$), the projection data may be collected. During the sampling off-stage (e.g., $T_{view-C}$), the projection data may not need to be collected. The processing device 140 may cause the imaging device 110 to repeat the synchronous switching process for the kV and the mA illustrated in FIG. 14 until the dural energy imaging is completed. By adopting the synchronous switching process of FIG. 14, the scan dose caused by the dural energy imaging may be effectively reduced.

Example 6

FIG. 15 shows a sixth relation between a tube voltage (kV) and a tube current (mA) applied to a radiation source according to some embodiments of the present disclosure. As illustrated in FIG. 15, the off-stage of mA may be classified to a short off-stage of mA and a long off-stage of mA. The time duration of the short off-stage is less than the time duration of the long off-stage. A first on-stage of mA may correspond to the time duration including the low energy voltage plateau duration represented by a solid line in the kV switching waveform. The first on-stage of mA may include two consecutive time durations of low energy projection (e.g., $T_{view-l}$). A second on-stage of mA may correspond to the time duration including the high energy voltage plateau duration represented by a solid line in the kV switching waveform. The second on-stage of mA may include two consecutive time durations of high energy projection (e.g., $T_{view-h}$). A short off-stage of mA may correspond to the time duration including the kV rising edge. A long off-stage of mA may correspond to part of the low energy voltage plateau duration which is represented by a dashed line in the kV switching waveform. The first one-stage of mA, the short off-stage of mA, the second on-stage of mA and the long off-stage of mA may be repeated periodically during the dual energy imaging. In some embodiments, the sampling period may be correlated with the mA switching period. The sampling on-stage may correspond to the on-stage of mA, for example, two consecutive $T_{view-l}$ and/or two consecutive $T_{view-h}$. The sampling off-stage may include a short sampling off-stage corresponding to the short off-stage of mA, and a long sampling off-stage corresponding to the long off-stage of mA. According to the kV switching waveform and the mA switching period illustrated in FIG. 15, the dual energy imaging may be performed.

According to the waveforms of kV and mA illustrated in FIG. 15, during the kV is within the kV rising edge, the mA is within the short off-stage and the mA is switched off, so as to reduce the kV rise time. During the kV is within the kV falling edge, the mA is within the on-stage and the mA is switched on. The mA may be maintained at a high relatively rated mA value (e.g., 600 mA). The high mA may be used to effectively reduce the kV fall time. The actual kV switching waveform may close to the ideal kV switching waveform. Thereby the spectral energy separation may be improved accordingly. In addition, compared with the kV switching waveforms of FIG. 10a-FIG. 14, the low energy projection and low energy projection are not interleaved one by one, but in the form of two or more consecutive low energy projections followed by two or more consecutive high energy projections. In each switch, the kV rise time and the kV fall time are reduced effectively, so the total scan time may be reduced accordingly and the scan dose may be reduced significantly.

As described in connection with FIG. 10B, the grid voltage (not shown in FIG. 15) may be introduced to switch on/off mA. The switching of mA is synchronized with the switching of the grid voltage. The dual energy imaging may be performed by synchronously switching kV, mA and the grid voltage. Merely for illustration, the processing device 140 may cause the HVG to apply the kV to the radiation source 113 according to the kV switching waveform. The processing device 140 may cause the switching of grid voltage to switch on/off the mA. The switching period of the grid voltage may be synchronized with the mA switching period. For example, during the on-stage of mA, the processing device 140 may cause the grid voltage of the grid electrode to be at about zero, which may allow the electron emission of the cathode filament so that the mA may be maintained at a rated mA value. In some embodiments, the rated mA may be a relatively high mA value (e.g., 600 mA). As another example, during the off-stage of mA (e.g., the short off-stage of mA and the long off-stage of mA), the processing device 140 may cause the grid voltage of the grid electrode to be the negative cut-off voltage. Thus the electron emission of the cathode filament may be stopped due to the limitation of the negative grid voltage. The mA may be switched off accordingly, and there is no mA to be discharged. During the sampling on-stages (e.g., the two consecutive $T_{view-l}$ and the two consecutive $T_{view-h}$), the projection data may be collected. During the short and long sampling off-stages, the projection data may not need to be collected. The processing device 140 may cause the imaging device 110 to repeat the synchronous switching process for the kV and the mA illustrated in FIG. 15 until the dural energy imaging is completed. By adopting the synchronous switching process of FIG. 15, the scan dose caused by the dural energy imaging may be effectively reduced.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A non-transitory computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2003, Perl, COBOL 2002, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, e.g., an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities, properties, and so forth, used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. An imaging method implemented on a computing device having at least one processor and at least one non-transitory computer-readable storage medium, the method comprising:
   acquiring a tube voltage switching waveform for a radiation source of a medical device, the tube voltage switching waveform configured to direct an alternation between a high energy tube voltage and a low energy tube voltage that are applied to the radiation source;
   determining a tube current switching period based on the tube voltage switching waveform, the tube current switching period indicative of an on-off state of the tube current applied to the radiation source;
   determining a sampling period correlated with the tube current switching period;
   acquiring projection data according to the sampling period, wherein the projection data includes first projection data under the high energy tube voltage and second projection data under the low energy tube voltage, and the projection data is generated according to the on-off state of a tube current indicated by the tube current switching period; and
   reconstructing an image based on the acquired projection data.

2. The method of claim 1, wherein:
   the alternation between a high energy tube voltage and a low energy tube voltage is represented by a rising edge, a falling edge, a low energy voltage plateau duration and a high energy voltage plateau duration of the tube voltage switching waveform; and the on-off state of the tube current consisting of an on-stage of the tube current switching period and an off-stage of the tube current switching period and the on-stage and the off-stage alternate.

3. The method of claim 2, wherein the determining a tube current switching period based on the tube voltage switching waveform further includes:

determining that the tube current is within the on-stage of the tube current switching period in response to occurrence of the falling edge of the tube voltage.

4. The method of claim 2, wherein the determining a tube current switching period based on the tube voltage switching waveform further includes:

determining that the tube current is within the off-stage of the tube current period in response to occurrence of the tube voltage between a first predetermined time of the low energy voltage plateau duration and a second predetermined time of the low energy voltage plateau duration.

5. The method of claim 2, wherein the determining a tube current switching period based on the tube voltage switching waveform further includes:

determining that the tube current is within the off-stage of the tube current period in response to occurrence of the tube voltage between a third predetermined time of the low energy voltage plateau duration and a fourth predetermined time of the rising edge.

6. The method of claim 2, wherein the determining a tube current switching period based on the tube voltage switching waveform further includes:

determining that the tube current is within the off-stage of the tube current period in response to occurrence of the tube voltage between a fifth predetermined time of the low energy voltage plateau duration and a sixth predetermined time of the high energy voltage plateau duration.

7. The method of claim 2, wherein the determining a tube current switching period based on the tube voltage switching waveform further includes:

determining that the tube current is within the off-stage of the tube current period in response to occurrence of the tube voltage between a seventh predetermined time of the high energy voltage plateau duration and an eighth predetermined time of the high energy voltage plateau duration.

8. The method of claim 2, wherein the off-stage of the tube current switching period includes a short off-stage and a long off-stage, the determining a tube current switching period based on the tube voltage switching waveform further includes:

determining that the tube current is on the short off-stage in response to occurrence of the tube voltage between a ninth predetermined time of the rising edge and a tenth predetermined time of the rising edge; and determining that the tube current is within the long off-stage in response to occurrence of the tube voltage between an eleventh predetermined time of the low energy voltage plateau duration and a twelfth predetermined time of the low energy voltage plateau duration.

9. The method of claim 2, wherein the determining a sampling period correlated with the tube current switching period further includes:

determining, based on the on-off state of the tube current, a sampling on-stage and a sampling off-stage respectively, wherein the sampling on-stage includes at least part of the time duration corresponding to the on-stage of the tube current switching period.

10. The method of claim 9, wherein the determining a sampling period correlated with the tube current switching period further includes:

determining that the sampling off-stage is between a thirteenth predetermined time of the low energy voltage plateau duration and a fourteenth predetermined time of the low energy voltage plateau duration.

11. The method of claim 9, wherein the determining a sampling period correlated with the tube current switching period further includes:

determining that the sampling off-stage is between a fifteenth predetermined time of the falling edge and a sixteenth predetermined time of the low energy voltage plateau duration.

12. The method of claim 9, wherein the determining a sampling period correlated with the tube current switching period further includes:

determining that the sampling off-stage is between a seventh predetermined time of the low energy voltage plateau duration and an eighteenth predetermined time of the rising edge.

13. The method of claim 9, wherein the determining a sampling period correlated with the tube current switching period further includes:

determining that the sampling off-stage is between a nineteenth predetermined time of the high energy voltage plateau duration and a twentieth predetermined time of the falling edge.

14. The method of claim 9, wherein the determining a sampling period correlated with the tube current switching period further includes:

determining that the sampling off-stage is between a twenty-first predetermined time of the high energy voltage plateau duration and a twenty-second predetermined time of the falling edge.

15. The method of claim 9, wherein the sampling off-stage includes a short sampling off-stage and a long sampling off-stage, the determining a sampling period correlated with the tube current switching period further includes:

determining that the short sampling off-stage is between a twenty-third predetermined time of the rising edge and a twenty-fourth predetermined time of the rising edge; and determining that the long sampling off-stage is between a twenty-fifth predetermined time of the falling edge and a twenty-sixth predetermined time of the low energy voltage plateau duration.

16. An imaging system, comprising:

at least one non-transitory storage medium including a set of instructions for reconstructing a computed tomography (CT) image; and at least one processor configured to communicate with the at least one non-transitory storage medium, wherein when executing the set of instructions, the system is directed to:

acquire a tube voltage switching waveform for a radiation source of a medical device, the tube voltage switching waveform configured to direct an alternation between a high energy tube voltage and a low energy tube voltage that are applied to the radiation source;

determine a tube current switching period based on the tube voltage switching waveform, the tube current switching period indicative of an on-off state of the tube current applied to the radiation source;

determine a sampling period correlated with the tube current switching period;

acquire projection data according to the sampling period, wherein the projection data includes first projection data under the high energy tube voltage and second projection data under the low energy tube voltage, and the projection data is generated according to the on-off state of a tube current indicated by the tube current switching period; and reconstruct an image based on the acquired projection data.

17. The imaging system of claim 16, wherein:

the alternation between a high energy tube voltage and a low energy tube voltage is represented by a rising edge, a falling edge, a low energy voltage plateau duration and a high energy voltage plateau duration of the tube voltage switching waveform; and the on-off state of the tube current consisting of an on-stage of the tube current switching period and an off-stage of the tube current switching period and the on-stage and the off-stage alternate.

18. The imaging system of claim 16, wherein to determine a tube current switching period based on the tube voltage switching waveform, the system is further directed to:

determine that the tube current is within the on-stage of the tube current switching period in response to occurrence of the falling edge of the tube voltage.

19. A non-transitory computer readable medium embodying a computer program product, the computer program product comprising instructions configured to cause a computing device to:

acquire a tube voltage switching waveform for a radiation source of a medical device, the tube voltage switching waveform configured to direct an alternation between a high energy tube voltage and a low energy tube voltage that are applied to the radiation source;

determine a tube current switching period based on the tube voltage switching waveform, the tube current switching period indicative of an on-off state of the tube current applied to the radiation source;

determine a sampling period correlated with the tube current switching period;

acquire projection data according to the sampling period, wherein the projection data includes first projection data under the high energy tube voltage and second projection data under the low energy tube voltage, and the projection data is generated according to the on-off state of a tube current indicated by the tube current switching period; and reconstruct an image based on the acquired projection data.

20. The non-transitory computer readable medium of claim 19, wherein:

the alternation between a high energy tube voltage and a low energy tube voltage is represented by a rising edge, a falling edge, a low energy voltage plateau duration and a high energy voltage plateau duration of the tube voltage switching waveform; and the on-off state of the tube current consisting of an on-stage of the tube current switching period and an off-stage of the tube current switching period and the on-stage and the off-stage alternate.

\* \* \* \* \*